US012576046B2

(12) United States Patent
Novak et al.

(10) Patent No.: US 12,576,046 B2
(45) Date of Patent: Mar. 17, 2026

(54) AQUEOUS PAEDIATRIC RETINOL FORMULATIONS

(71) Applicant: ORPHANIX GMBH, Linz (AT)

(72) Inventors: Philipp Novak, Linz (AT); Christian Seliger, Wielenbach (DE); Jochen Bauer, Holzkirchen (DE)

(73) Assignee: ORPHANIX GMBH, Linz (AT)

( * ) Notice: Subject to any disclaimer, the term of this patent is extended or adjusted under 35 U.S.C. 154(b) by 1103 days.

(21) Appl. No.: 17/296,571

(22) PCT Filed: Nov. 26, 2019

(86) PCT No.: PCT/EP2019/082510
§ 371 (c)(1),
(2) Date: May 25, 2021

(87) PCT Pub. No.: WO2020/109272
PCT Pub. Date: Jun. 4, 2020

(65) Prior Publication Data
US 2022/0000802 A1    Jan. 6, 2022

(30) Foreign Application Priority Data
Nov. 26, 2018    (EP) ..................................... 18208340

(51) Int. Cl.
| | |
|---|---|
| *A61K 31/07* | (2006.01) |
| *A61K 9/00* | (2006.01) |
| *A61K 9/107* | (2006.01) |
| *A61K 47/34* | (2017.01) |

(52) U.S. Cl.
CPC ............ *A61K 31/07* (2013.01); *A61K 9/0019* (2013.01); *A61K 9/107* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 3,070,499 | A | 12/1962 | Mullins et al. |
| 3,708,583 | A | 1/1973 | Winstrom et al. |
| 4,022,913 | A | 5/1977 | Newmark |
| 4,075,333 | A | 2/1978 | Josse |
| 4,840,970 | A | 6/1989 | Ohasi et al. |
| 5,891,907 | A | 4/1999 | Kolter et al. |
| 5,925,684 | A | 7/1999 | Schweikert et al. |
| 2010/0160456 | A1 | 6/2010 | Quiroga |
| 2014/0005274 | A1 | 1/2014 | Nakata |
| 2015/0018416 | A1 | 1/2015 | Komurasaki et al. |
| 2016/0000727 | A1 | 1/2016 | Frantsits |
| 2018/0147174 | A1 | 5/2018 | Brito De La Fuente et al. |

FOREIGN PATENT DOCUMENTS

| | | | |
|---|---|---|---|
| AT | 489938 | T | 12/2010 |
| CN | 101579310 | A | 11/2009 |
| CN | 101703468 | A | 5/2010 |
| CN | 102743394 | A | 10/2012 |
| CN | 103349666 | A | 10/2013 |
| CN | 105663144 | A | 6/2016 |
| CN | 105663145 | A | 6/2016 |
| CN | 106420793 | A | 2/2017 |
| CN | 106727310 | A | 5/2017 |
| CN | 107115349 | A | 9/2017 |
| CN | 107260669 | A | 10/2017 |
| CN | 109010264 | A | 12/2018 |
| EP | 0 473 159 | A1 | 3/1992 |
| EP | 1 698 329 | A1 | 9/2006 |
| EP | 3 297 604 | A1 | 3/2018 |
| EP | 3 297 606 | A1 | 3/2018 |
| GB | 748221 | A | 4/1956 |
| GB | 946086 | A | 1/1964 |
| GB | 1464797 | A | 2/1977 |
| GB | 1471797 | A | 4/1977 |
| HK | 1197018 | A1 | 1/2015 |
| JP | S61189216 | A | 8/1986 |
| JP | H 05186343 | A | 7/1993 |
| JP | 3199475 | B2 | 8/2001 |
| KR | 20010055736 | A | 7/2001 |
| KR | 20090083322 | * | 8/2009 |
| WO | WO-96/36340 | A1 | 11/1996 |
| WO | WO 98/30205 | A1 | 7/1998 |
| WO | WO 006112 | A1 | 10/2000 |
| WO | WO-2006/130048 | A2 | 12/2006 |
| WO | WO-2014/006215 | A1 | 1/2014 |
| WO | WO 2015/188874 | A1 | 12/2015 |
| WO | WO 2016/188876 | A1 | 12/2016 |
| ZA | 201300444 | B | 9/2013 |

OTHER PUBLICATIONS

Lidgate et al., Sterile Filtration of a Parenteral Emulsion, Pharmaceutical Research, vol. 9, No. 7, 1992) (Year: 1992).*
Sharma et al., Role of microemuslsions in advanced drug delivery, Artificial Cells, Nanomedicine, and Biotechnology 2016; 44: 1177-1185) (Year: 2016).*
Rakshasbhuvankar et al., Enteral vitamin A for reducing severity of bronchopulmonary dysplasia in extremely preterm infants: a randomised controlled trial, Pediatrics 17:204, published online Dec. 16, 2017 (Year: 2017).*
Hennelly et al., An Update on the Prevention and Management of Bronchopulmonary Dysplasia Pediatric Health, Medicine and Therapeutics 2021:12 405-419 (Year: 2021).*
Anonymous: Nepalm Vitamin A; Annex I, Summary of Product Features , pp. 1-3 (2008).
Anonymous: "AQUASOL A-vitamin a palmitate injection, solution, Hospira, Inc.", pp. 1-11 (2018).

(Continued)

*Primary Examiner* — Bennett M Celsa
*Assistant Examiner* — Edwin Coleman Mitchell
(74) *Attorney, Agent, or Firm* — White & Case LLP

(57) ABSTRACT

The present application relates to an aqueous pharmaceutical composition for use as a paediatric medicament in the treatment or prevention of vitamin A deficiency or a vitamin A deficiency-associated disease.

11 Claims, 1 Drawing Sheet

(56)  References Cited

OTHER PUBLICATIONS

BASF: "Solutol HS15—Technical Information," pp. 1-8 (2003).
International Preliminary Report on Patentability, PCT/EP2019/082510, dated May 25, 2021 (9 pages).
Mandal et al., "Polymeric micelles for ocular drug delivery: From structural frameworks to recent preclinical studies," J. Control Release, vol. 248: 96-116 (2017).
Pacifici, Maria G., "Effects of Vitamin A in Neonates and Young Infants," Int. J. Pediatr., vol. 4(2): 1139-1354 (2016).
Grotz et al., "Nanoscale Kolliphor$^R$ HS 15 micelles to minimize rifampicin self-aggregation in aqueous media," Journal of Drug Delivery Science and Technology, vol. 41:1-6 (2017).
Liu, L et al., "Kolliphor$^R$ HS 15 Micelles for the Delivery of Coenzyme Q10: Preparation, Characterization, and Stability," AAPS PharmSciTech, vol. 17(3):757-766 (2015).
German Pharmacopoeia 10, Appendix, pp. 731-732 (1991) (total 4 pages).
Lorenz and Doenicke (1986). "Problems with Solubilizers in the Intravenous Use of Hypnotics," Anaesthesiology and Intensive Care Medicine, vol. 188. Springer, Berlin, Heidelberg (1986). (https://link.springer.com/chapter/10.1007/978-3-642-71269-2_10).
Cremophor, Meyler's Side Effects of Drugs, 16th edition, (1 page) (2016).
Nan, Anjan, "A worldwide yearly survery of new data in adverse drug reactions, Cremophor", Side Effect of Drugs Annual, (1 page) (2015).
Reinhart and Bauer, "Parenteral preparations of Substances that are Difficult to Dissolve in Water," Krankenhauspharmazie, Hospital Pharmacy, vol. 15(9): 529-533 (1994).
Voigt, R., "Solution Manufacturing," Pharmazeutische Technologie, vol. 7, Chapter 20, pp. 471-477 (1993).
Aquasol A ™ Parental—Hospira, Inc. "This is a Sterile Product for Intramuscular Injection", (4 pages) (Mar. 2018).
Arrowsmith et al., "Morbidity and Mortality Among Low Birth Weight Infants Exposed to an Intravenous Vitamin E Product, E-Ferol", Pediatrics, vol. 83(2); 244-249 (1989).
Baeckert et al., "Vitamin concentrations in very low birth weight infants given vitamins intravenously in a lipid emulsion: Measurement of vitamins A, D, and E and riboflavin," J. Pediatr, vol. 113(6): 1057-1065 (1988).
Balistreri et al., "Lessons from the E-Ferol tragedy," Pediatrics, vol. 78(3): 503-506 (1986).
BASF, Kolliphor® HS 15- The potent nonionic solubilizer, 2 pages (2018).
BASF; Pharma Ingredients & Services; SolutoIR HS 15; A nonionic solubilizer. Technical Information; 8 pages (Aug. 2010).
Brandt et al., "Serum vitamin A in premature and term neonates," The Journal of Pediatrics, vol. 92(1): 101-104 (1978).
Cuzzolin, Laura, "Neonates exposed to excipients: concern about safety," Journal of Pediatric and Neonatal Individualized Medicine, vol. 7(1): e070112 (2017).
Darlow et al., "Vitamin A supplementation to prevent mortality and short- and long-term morbidity in very low birth weight infants," Cochrane Library, Cochrane Database Systematic Reviews, CD000501. pub4, 78 pages (2016).
DSM. Product Information—Vitamin A palmitate, 3 pages (2015).
Graham, Susan, "European Study of Neonatal Exposure to Excipients (ESNEE)", Infant, vol. 7(6): 196-199 (2011).
Greene et al., "Intravenous vitamins for very-low-birth-weight infants," Journal of the American College of Nutrition, vol. 10(4): 281-288 (1991).
Greene et al., "Persistently Low Blood Retinol Levels During and After Parenteral Feeding of Very Low Birth Weight Infants: Examination of Losses Into Intravenous Administration Sets and a Method of Prevention by Addition to a Lipid Emulsion," Pediatrics, vol. 79(6): 894-900 (1987).
Haas et al., "Losses of vitamin A and E in parenteral nutrition suitable for premature infants," European Journal of Clinical Nutrition, vol. 56(9): 906-912 (2002).

Inder et al., "Clinical and laboratory observations. Vitamin A and E status in very low birth weight infants: Development of an improved parental delivery system," The Journal of Pedriatrics, vol. 126(1): 128-132 (1995).
Kuwahara et al., "Effects of lipid emulsion and multivitamins on the growth of microorganisms in peripheral parenteral nutrition solutions," International Journal of Medical Sciences, vol. 10(9): 1079-1084 (2013).
Kuwahara et al., "Growth of Microorganisms in Total Parenteral Nutrition Solutions Containing Lipid," International Journal of Medical Sciences, vol. 7(3): 101-109 (2010).
Lorenz et al., Histamine release and hypotensive reactions in dogs by solubilizing agents and fatty acids: analysis of various components in cremophor El and development of a compound with reduced toxicity, Agents and Actions, vol. 12(1-2): 64-80 (1982).
Lu et al., Systemic delivery of alpha-asarone with Kolliphor HS 15 improves its safety and therapeutic effect on asthma Drug Delivery, vol. 22(3): 266-275 (2015).
Mactier et al., "Vitamin A Supplementation Improves Retinal Function in Infants at Risk of Retinopathy of Prematurity," The Journal of Pediatrics, vol. 160(6): 954-959.e1 (2012).
Mactier, H., "Vitamin A for preterm infants; where are we now," Seminars in Fetal Neonatal Medicine, vol. 18: 166-171 (2013).
Martindale Pharmacopea: The Complete Drug Reference 36th Edition- Nonionic Durfactants, pp. 1914-1921; Published by the Pharmaceutical Press An imprint of RPS Publishing. (2009).
McClements, D. J., "Nanoemulsions versus microemulsions: terminology, differences, and similarities," Soft Matter, vol. 8(6): 1719-1729 (2012).
Metsvaht et al., Presentation: European Study of Neonatal Exposure to Excipients Excipients (ESNEE); 52 Pages (Dec. 4, 2012).
Mystery of the E-Ferol syndrome. Nutritional Reviews, vol. 45(3): 76-77 (1987).
Nepalm, Vitamin A Nepalm 100.000 IU /2ML injectable solution. Leaflet Information for the User (2014).
New Zealand Data Sheet (http://www.medsafe.govt.nz/profs/datasheet/v/VitalipidNinj.pdf); 6 pages (2019).
Ong, D. E., & Page, D. L., "Cellular retinol-binding protein (type two) is abundant in human small intestine," Journal of Lipid Research, vol. 28(6): 739-745 (1987).
Peeples et al., Vitamin A status of preterm infants during infancy; Am. J. Clin. Nutr., vol. 53: 1455 to 1459 (1991).
Pramanick et al., "Excipient Selection In Parenteral Formulation Development," Pharma Times, vol. 45(3): 65-77 (2013).
Riggle et al., Decrease of available vitamin A in parenteral nutrition solutions,: Journal of Parenteral and Enteral Nutrition, vol. 10(4): 388-392 (1986).
Shenai et al., "Plasma vitamin A and retinol-binding protein in premature and term neonates," Journal of Pediatrics, vol. 99(2): 302-305 (1981).
Shenai et al., "Vitamin A delivery from parental alimentation solution," Brief Clinical and Laboratory Observations; vol. 99(4): 661-663 (1981).
Vitamin A Palmitate -Cambridge Pharmaceuticals; p. 452; British National Formulary, vol. 41, (Mar. 2001).
Wardle et al., "Randomised controlled trial of oral vitamin A supplementation in preterm infants to prevent chronic lung disease," Archives of Disease in Childhood-Fetal and Neonatal Edition, vol. 84(1): F9-F13 (2001).
Werkman et al., "Effect of vitamin A supplementation of intravenous lipids on early vitamin A intake and status of premature infants," American Journal of Clinical Nutrition, vol. 59(3): 586-592 (1994).
Meyer-Boehm, K. et al., "Traditional Medicine Meets Modern Excipients," 10 pages (2012).
Moghimi et al., "Causative factors behind poloxamer 188 (Pluronic F68, Flocor™)-induced complement activation in human sera. A protective role against poloxamer-mediated complement activation by elevated serum lipoprotein levels," Science Direct, Biochimica et Biophysica Acta, 1689: 103-113 (2004).
Roethlisberger et al., "If Euhydric and Isotonic Do Not Work, What Are Acceptable pH and Osmolality for Parenteral Drug Dosage

(56) References Cited

OTHER PUBLICATIONS

Forms?", Journal of Pharmaceutical Sciences; vol. 106(2017):446-456 (Available Online Nov. 23, 2016).
U.S. Food & Drug Administration; Search Orphan Drug Designations and Approvals; Retinol Palmitate; Prevention of bronchopulmonary dysplasia; date designated Aug. 8, 2016 (https://www.accessdata.fda.gov/scripts/opdlisting/oopd/detailedIndex.cfm?cfgridkey=525116) (1 page).
U.S. Food & Drug Administration: Search Orphan Drug Designations and Approvals; Retinol Palmitate (vitamin A palmitate); Prevention of retinopathy of prematurity (ROP); date designated Jun. 28, 2017. (https://www.accessdata.fda.gov/scripts/opdlisting/oopd/detailedIndex.cfm?cfgridkey=583417) (1 page).
European Medicines Agency; "Public summary of opinion on orphan designation; Retinol for the prevention of bronchopulmonary dysplasia" (Sep. 23, 2014) (https://www.ema.europa.eu/en/documents/orphan-designation/eu3141307-public-summary-opinion- orphan-designation-retinol-prevention-bronchopulmonary-dysplasia_en.pdf ) (4 pages).
European Commission; Community Register of orphan medicinal products; Product Information; Product Name and Designation No. EU/3/17/1895); Retinol (2017) (https://ec.europa.eu/health/documents/community-register/html/o1895.htm) (1 page).
Ehrenkranz R, Walsh M, Vohr B, et al. Validation of the National Institutes of Health consensus definition of bronchopulmonary dysplasia. Pediatrics 2005; 116(6):1353-60. DOI: 10.1542/peds.2005-0249.
Norman M, Hallberg B, Abrahamsson T, et al. Association Between Year of Birth and 1-Year Survival Among Extremely Preterm Infants in Sweden During 2004-2007 and 2014-2016. JAMA 2019;321(12):1188-1199. DOI: 10.1001/jama.2019.2021.
Stoll BJ, Hansen NI, Bell EF, et al. Trends in Care Practices, Morbidity, and Mortality of Extremely Preterm Neonates, 1993-2012. JAMA 2015;314(10):1039-51. DOI: 10.1001/jama.2015. 10244.
Bancalari E, Jain D. Bronchopulmonary Dysplasia: 50 Years after the Original Description. Neonatology 2019;115(4): 384-391. DOI: 10.1159/000497422.
Schmidt B, Roberts RS, Davis PG, et al. Prediction of Late Death or Disability at Age 5 Years Using a Count of 3 Neonatal Morbidities in Very Low Birth Weight Infants. J Pediatr 2015; 167(5):982-6 e2. DOI: 10.1016/j.jpeds.2015.07.067.
Thunqvist P, Tufvesson E, Bjermer L, et al. Lung function after extremely preterm birth-A population-based cohort study (EXPRESS). Pediatr Pulmonol 2018;53(1):64-72. DOI: 10.1002/ppul.23919.
Alvarez-Fuente M, Arruza L, Muro M, et al. The economic impact of prematurity and bronchopulmonary dysplasia. Eur J Pediatr 2017. DOI: 10.1007/s00431-017-3009-6.
Hwang JS, Rehan VK. Recent Advances in Bronchopulmonary Dysplasia: Pathophysiology, Prevention, and Treatment. Lung 2018; 196(2):129-138. DOI: 10.1007/s00408-018-0084-z.
Schmidt B, Roberts R, Davis P, et al. Caffeine therapy for apnea of prematurity. N Engl J Med 2006;354(20):2112-21. DOI: 10.1056/NEJMoa054065.
Doyle LW, Cheong JL, Ehrenkranz RA, Halliday HL. Early (< 8 days) systemic postnatal corticosteroids for prevention of bronchopulmonary dysplasia in preterm infants. The Cochrane database of systematic reviews 2017;10:Cd001146. (In eng). DOI: 10.1002/14651858.CD001146.pub5.
Timoneda J, Rodríguez-Fernández L, Zaragozá R, et al. Vitamin A Deficiency and the Lung. Nutrients 2018; 10(9). DOI: 10.3390/nu10091132.
Fraslon C, Bourbon J. Retinoids control surfactant phospholipid biosynthesis in fetal rat lung. Am J Physiol 1994;266(6 Pt 1):L705-12. (http://www.ncbi.nlm.nih.gov/entrez/query.fcgi?cmd=Retrieve&db=PubMed&dopt=Citation&list_uids=8023960).
McGowan S, Takle E, Holmes A. Vitamin A deficiency alters the pulmonary parenchymal elastic modulus and elastic fiber concentration in rats. Respir Res 2005;6:77. DOI: 10.1186/1465-9921-6-77.

Esteban-Pretel G, Marin MP, Renau-Piqueras J, Sado Y, Barber T, Timoneda J. Vitamin A deficiency disturbs collagen IV and laminin composition and decreases matrix metalloproteinase concentrations in rat lung. Partial reversibility by retinoic acid. J Nutr Biochem 2013;24(1):137-45. DOI: 10.1016/j.jnutbio.2012.03.010.
Esteban-Pretel G, Marin MP, Renau-Piqueras J, Barber T, Timoneda J. Vitamin A deficiency alters rat lung alveolar basement membrane: reversibility by retinoic acid. J Nutr Biochem 2010;21(3):227-36. DOI: 10.1016/j.jnutbio.2008.12.007.
Zachman R. Retinol (vitamin A) and the neonate: special problems of the human premature infant. The American journal of clinical nutrition 1989 (http://aich.nutrition.org/content/50/3/413.short).
Spears K, Cheney C, Zerzan J. Low plasma retinol concentrations increase the risk of developing bronchopulmonary dysplasia and long-term respiratory disability in very-low-birth-weight infants. The American journal of clinical nutrition 2004; 80(6): 1589-94. (http://www.ncbi.nim.nih.gov/entrez/query.fcgi?cmd=Retrieve&db=PubMed&dopt=Citation&list_uids=15585773).
Mactier H, Weav. Vitamin A and preterm infants: what we know, what we don't know, and what we need to know. Archives of Disease in Childhood-Fetal and Neonatal Edition 2005;90(2):F103-F108. (http://fn.bmi.com/content/84/1/F9.full).
Rush M, Shenai J, Parker R, Chytil F. Intramuscular versus enteral vitamin A supplementation in very low birth weight neonates. J Pediatr 1994;125(3):458-62. (http://www.ncbi.nim.nih.gov/entrez/query.fcgi?cmd=Retrieve&db=PubMed&dopt=Citation&list_uids=8071758).
Wardle S, Hughes A, Chen S, Shaw N. Randomised controlled trial of oral vitamin A supplementation in preterm infants to prevent chronic lung disease. Archives of Disease in Childhood-Fetal and Neonatal Edition 2001;84(1):F9-F13. (http://fn.bmi.com/content/84/1/F9.full).
Garofoli F, Mazzucchelli I, Decembrino L, et al. Levels and effectiveness of oral retinol supplementation in VLBW preterm infants. Int J Immunopathol Pharmacol 2018;32:2058738418820484. DOI: 10.1177/2058738418820484.
Meyer S, Bay J, Franz AR, et al. Early postnatal high-dose fat-soluble enteral vitamin A supplementation for moderate or severe bronchopulmonary dysplasia or death in extremely low birthweight infants (NeoVitaA): a multicentre, randomised, parallel-group, double-blind, placebo- controlled, investigator-initiated phase 3 trial. Lancet Respir Med 2024;12(7):544-555. DOI: 10.1016/S2213-2600(24)00073-0.
Kennedy K, Stoll B, Ehrenkranz R, et al. Vitamin A to prevent bronchopulmonary dysplasia in very-low-birth-weight infants: has the dose been too low? The NICHD Neonatal Research Network. Early Hum Dev 1997;49(1):19-31. (https://www.ncbi.nlm.nih.gov/entrez/query fogi?cmd=Retrieve&db=PubMed&dopt=Citation&list_ui ds=9179535).
Darlow B, Graham P, Rojas-Reyes M. Vitamin A supplementation to prevent mortality and short- and long-term morbidity in very low birth weight infants. Cochrane Database Syst Rev2016:CD000501.
Balistreri W, Farrell M, Bove K. Lessons from the E-Ferol tragedy. Pediatrics 1986;78(3):503-6. (http://www.ncbi.nim.nih.gov/entrez/query.fcgi?cmd=Retrieve&db-PubMed&dopt=Citation&list_uids=3748688).
Johansson S, Allegaert K. Parenteral retinol (vitamin A) supplementation, 5000 IU three times a week for four weeks, and risk of death or bronchopulmonary dysplasia in very low birth weight infants. 2023 (Confidential Report—prepared and provided for Aspire Pharma Ltd).
Poets C, Zimmermann L, Hellstrom-Westas L, et al. Prevention of Bronchopulmonary Dysplasia (BPD). (https://newborn-health-standards.org/standards/standards-english/medical-care-clinical-practice/prevention-of-bronchopulmonary-dysplasia-bpd/).
McEvoy C, Jain L, Schmidt B, Abman S, Bancalari E, Aschner J. Bronchopulmonary dysplasia: NHLBI Workshop on the Primary Prevention of Chronic Lung Diseases. Ann Am Thorac Soc 2014;11 Suppl 3:S146-53. DOI: 10.1513/AnnalsATS.201312-424LD.
Mactier H, McCulloch D, Hamilton R, et al. Vitamin A supplementation improves retinal function in infants at risk of retinopathy of prematurity. J Pediatr 2012;160(6):954-9.e1. DOI: 10.1016/j.jpeds.2011.12.013.

(56)               References Cited

OTHER PUBLICATIONS

Wang L, Shi P, Xu Z, et al. Up-regulation of VEGF by retinoic acid during hyperoxia prevents retinal neovascularization and retinopathy. Invest Ophthalmol Vis Sci 2014;55(7):4276-87. DOI: 10.1167/iovs. 14-14170.

Zhou M, Duan PC, Li DL, et al. Efficacy comparison of 21 interventions to prevent retinopathy of prematurity: a Bayesian network meta-analysis of randomized controlled trials. Eye (Lond) 2024;38(5):877-884. DOI: 10.1038/s41433-023-02796-2.

* cited by examiner

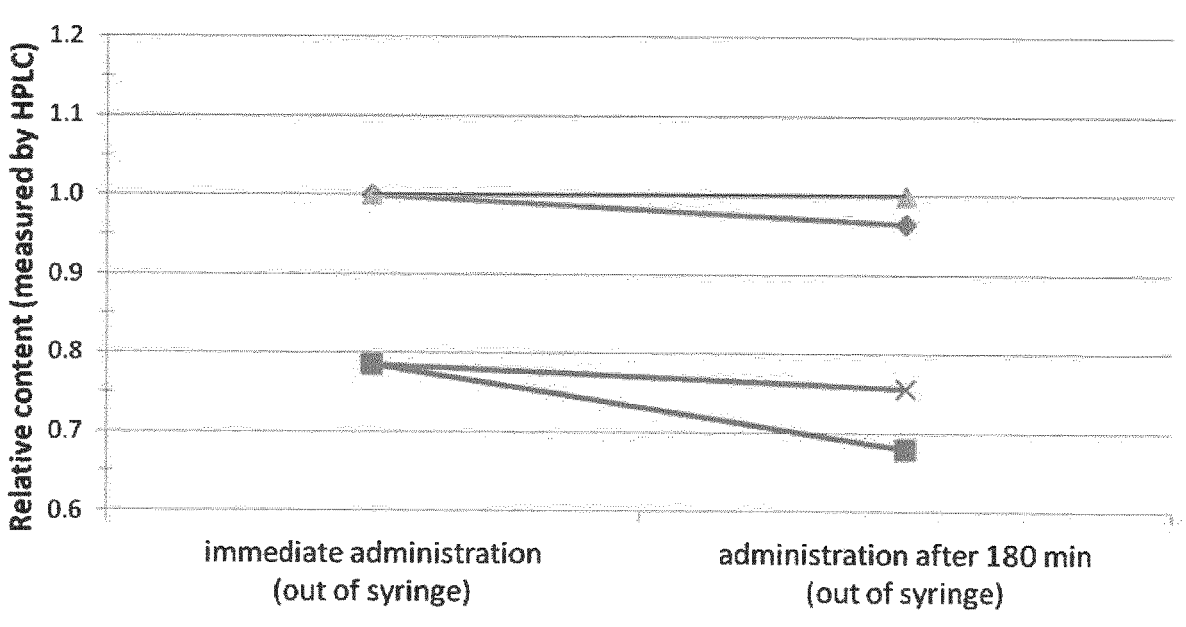
RELATIVE VITAMIN A CONTENT - HOLDING TIME
1 ML SYRINGE

1

AQUEOUS PAEDIATRIC RETINOL FORMULATIONS

CROSS-REFERENCE TO RELATED APPLICATIONS

This application is a national stage filing under 35 U.S.C. § 371 of International Application No. PCT/EP2019/082510, filed Nov. 26, 2019, which claims the benefit of priority of European Application No. 18208340.2, filed Nov. 26, 2018. The specifications of each of the foregoing applications are hereby incorporated by reference in their entirety. International Application PCT/EP2019/082510 was published under PCT Article 21 (2) in English.

FIELD OF THE INVENTION

The present invention relates to aqueous paediatric retinol formulations, particularly an aqueous pharmaceutical composition as defined in the claims, for use as a paediatric medicament in the treatment or prevention of vitamin A deficiency or a vitamin A deficiency-associated disease.

BACKGROUND OF THE INVENTION

Augmented vitamin A supply is required in patients with limited or no gastrointestinal uptake due to nutritional imbalances, prematurity of the gastrointestinal tract, insufficient bile production and/or other underlying diseases. This particularly applies to diseases such as bronchopulmonary dysplasia, retinopathy of prematurity, liver disease with cholestasis, biliary atresia, diseases associated with liver transplantation, primary biliary cirrhosis, conjunctival xerosis, Bitot's spot, corneal xerosis, corneal ulceration and xerosis, keratomalacia, night blindness, dark adaptation, xerophthalmic scars of cornea, ocular manifestations, xerophthalmia nos, measles, or kwashiorkor. The parenteral supply of vitamin A has been described to be beneficial to prevent or treat such diseases.

For over 35 years the majority of cases of generalized deficiency of retinol (vitamin A) has been found in premature infants (NPTL1). Preterm infants are born with inadequate body stores of vitamin A in the foetal liver as well as in the retina. In addition to low tissue concentrations preterm infants have low plasma concentrations of both retinol and its essential carrier retinal binding protein.

Plasma concentrations of retinol remain low during the infant's stay in the neonatal unit and this even persists into later infancy (NPTL2, NPTL3, NPTL4, NPTL5). Thus, preterm infants are particularly prone to diseases associated with vitamin A deficiency, such as diseases of the respiratory and gastrointestinal tracts, as well as diseases of the eye, such as retinopathy of prematurity (ROP).

If an infant is born prematurely, vitamin A accretion in utero is interrupted at this crucial stage and preterm neonates are deprived of much transplacental vitamin A acquisition, which is fundamental to build up sufficient vitamin A stores in the foetal liver and in the retina during the third trimester (NPTL3).

Oral retinol administration is typically ineffective in premature infants. This most vulnerable population thus requires a particular treatment modality as compared to more mature neonates. Given that preterm neonates with low birth weight are at high risk for various diseases as mentioned above and have low retinol stores at birth combined with inefficient enteral intake, they can particularly benefit from retinol administration and should thus be supplemented by a parenteral, age-appropriate dosage form of retinol, at least in early life (NPTL6).

More than one hundred years since the discovery of a 'fat-soluble factor A' present in animal fats and necessary for normal growth as well as the health of the corneal epithelium, vitamin A deficiency remains common in the developing world where it contributes significantly to infant mortality and morbidity. By contrast, in more affluent countries vitamin A deficiency is uncommon and almost exclusively confined to older subjects with significant malabsorptive disorders. The notable exception to this is the preterm infant population. Born with reduced stores of vitamin A, preterm infants require vitamin A for ongoing lung and retinal development. The generic term "vitamin A" includes a number of fat-soluble compounds, including retinol (the alcohol form), retinyl esters (retinol palmitate, retinol acetate, or retinol propionate), retinaldehyde, and retinoid acid (NPTL7).

The vitamin A compound most commonly used in parenteral formulations is the retinol ester retinol palmitate. In general, all vitamin A compounds are sensitive to oxygen, heat and light, and are therefore challenging to formulate and produce (NPTL8).

Vitamin A based emulsions for parenteral administration have been described, wherein the emulsions are free of polysorbates and polyoxyethylen/polyoxypropylene block copolymers (PTL1 and PTL2).

However, emulsions have many shortcomings in production and administration in intensive care: Sterile filtration is mostly not feasible in commercial production, typically the product has to be heat-sterilized which is problematic with heat sensitive ingredients such as retinal. Emulsions containing vitamin A typically are opaque and white-milky. They are prone to microbial contamination and any kind of impurities cannot be directly detected by staff producing the final product or by medical staff administering it in intensive care (NPTL9, NPTL10, NPTL20), which constitutes a further disadvantage. Moreover, as can be seen from the examples in PTL1 and PTL2, the manufacturing process for such emulsions is quite complex, even though the products exhibit limited stability.

Many non-ionic solubilizers have the potential to release histamine after parenteral administration. Histamine is the most important inflammatory mediator released by mast cells and basophiles when challenged during an allergic reaction, in which tachypnea, expiratory dyspnea and even spasm can be observed, and histamine plays a crucial role in anaphylaxis and the cause of death.

A commercially available product is "Vitamine A Nepalm" by Nepalm, France (NPTL26), which may be regarded as a micro-emulsion containing polyoxyethlene hydrogenated castor oil RH 40. This formulation is also free of polysorbates and polyoxyethylen/polyoxypropylene block copolymers (NPTL 11).

Another parenteral vitamin A product by Cambridge Pharmaceuticals (NPTL12), containing polyethoxylated castor oil, is no longer available. A further parenteral vitamin A formulation is AQUASOL A (NPTL14; NPTL27).

As emulsions cannot be sterilized by using sterile filters, they need to be heat sterilized which is a disadvantage particularly with heat sensitive substances such lipid soluble vitamins.

DESCRIPTION OF THE FIGURE

FIG. 1 Vitamin A output after syringe administration at different holding times. See Example 2.

SUMMARY OF THE INVENTION

As explained above, new-born infants, in particular pre-term infants, are prone to diseases associated with vitamin A deficiency, such as diseases of the respiratory tract resulting, e.g., in bronchopulmonary dysplasia (BPD), as well disease of the eye resulting, e.g., in retinopathy of prematurity (ROP).

There is thus an urgent and unmet need for a novel stable pharmaceutical formulation of vitamin A, which is suitable for intramuscular and intravenous administration and is free of excipients harmful to infants.

It is thus an object of the present invention to provide a stable formulation of vitamin A for the treatment or prevention of vitamin A deficiency or a vitamin A deficiency-associated disease specifically in the paediatric population. In this respect, it is a further object of the invention to provide a corresponding vitamin A formulation which does not contain any harmful excipients or solubilizers leading to anaphylaxis, which is suitable for intravenous or intramuscular administration, and which can be easily diluted.

Accordingly, the present invention provides an aqueous pharmaceutical composition for use as a paediatric medicament in the treatment or prevention of vitamin A deficiency or a vitamin A deficiency-associated disease, wherein the composition comprises:

retinol or a pharmaceutically acceptable ester thereof, one or more polyethylene glycol esters of hydroxystearic acid, and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less; and wherein the composition has an osmolality of about 100 to about 600 mOsm/kg.

The aqueous pharmaceutical composition according to the present invention is highly advantageous over emulsions of vitamin A, particularly in that it is clear/transparent, has low viscosity, and is thus easy to administer.

Clarity or transparency of the pharmaceutical composition is of particular importance as it allows the detection of lumps, coagula or particles during manufacturing or later at bed-site administration. If such lumps, coagula or particles were not easily detectable, as it is the case with emulsions, this would entail the risk of causing thrombi leading to serious and potentially life-threatening adverse events.

The aqueous pharmaceutical composition of the present invention is particularly well-suitable for neonates, and is free of potentially harmful excipients for neonates. Furthermore, its solubilizing agent is suitable for intravenous (IV) and intramuscular (IM) administration alike and has been found to have excellent local tolerance and releasing less histamine compared to other non-ionic solubilizer as used in other vitamin A formulations. It also exhibits enhanced long-term stability and has high optical clarity. In addition, it is dilutable, e.g., with 0.9% sodium chloride and 5% dextrose up to about 1:99, thus allowing for precise intravenous administration over time.

The composition according to the invention is furthermore advantageous in that it exhibits particularly low interaction with medical disposables such as infusion tubing, syringes and catheters.

The inventive composition contains micelles with a diameter of less than about 100 nm and can thus be sterilized by sterile filtration. This is advantageous as the composition according to the invention does consequently not require antimicrobial excipients. Accordingly, the aqueous pharmaceutical composition provided herein is preferably free of antimicrobial excipients.

The inventive composition is preferably supplied as a user-friendly, therapeutic regimen containing about 12 single unit doses, whereby re-use of the unit dose container can be avoided.

DETAILED DESCRIPTION OF THE INVENTION

As described above, the present invention provides an aqueous pharmaceutical composition for use as a paediatric medicament in the treatment or prevention of vitamin A deficiency or a vitamin A deficiency-associated disease, wherein the composition comprises:

retinol or a pharmaceutically acceptable ester thereof, one or more polyethylene glycol esters of hydroxystearic acid, and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less; and wherein the composition has an osmolality of about 100 to about 600 mOsm/kg.

Accordingly, the present invention relates to an aqueous pharmaceutical composition for use in the treatment or prevention of vitamin A deficiency or a vitamin A deficiency-associated disease in a human child, wherein the composition comprises:

retinol or a pharmaceutically acceptable ester thereof, one or more polyethylene glycol esters of hydroxystearic acid, and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less; and wherein the composition has an osmolality of about 100 to about 600 mOsm/kg.

The invention is likewise directed to the use of retinol or a pharmaceutically acceptable ester thereof in combination with one or more polyethylene glycol esters of hydroxystearic acid for the preparation of a paediatric medicament for the treatment or prevention of vitamin A deficiency or a vitamin A deficiency-associated disease, wherein the medicament is an aqueous pharmaceutical composition comprising:

retinol or a pharmaceutically acceptable ester thereof, one or more polyethylene glycol esters of hydroxystearic acid, and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less; and wherein the composition has an osmolality of about 100 to about 600 mOsm/kg.

The invention is also directed to the use of retinol or a pharmaceutically acceptable ester thereof in combination with one or more polyethylene glycol esters of hydroxystearic acid for the preparation of a medicament for the treatment or prevention of vitamin A deficiency or a vitamin A deficiency-associated disease in a human child, wherein the medicament is an aqueous pharmaceutical composition comprising:

retinol or a pharmaceutically acceptable ester thereof, one or more polyethylene glycol esters of hydroxystearic acid, and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less; and wherein the composition has an osmolality of about 100 to about 600 mOsm/kg.

Moreover, the present invention also provides a method of treating or preventing vitamin A deficiency or a vitamin A deficiency-associated disease, the method comprising administering an aqueous pharmaceutical composition to a subject in need thereof, wherein the composition comprises:

retinol or a pharmaceutically acceptable ester thereof, one or more polyethylene glycol esters of hydroxystearic acid, and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less; and wherein the composition has an osmolality of about 100 to about 600 mOsm/kg.

It will be understood that the method comprises the administration of a therapeutically effective amount of the aqueous pharmaceutical composition; in other words, it comprises the administration of the aqueous pharmaceutical composition comprising a therapeutically effective amount of retinol or a pharmaceutically acceptable ester thereof.

The present invention will be described in more detail in the following.

The Retinol or Pharmaceutically Acceptable Ester Thereof

The aqueous pharmaceutical composition of the present invention contains retinol and/or one or more pharmaceutically acceptable retinol esters. In other words, the aqueous pharmaceutical composition may contain only retinol, only a retinol ester, a combination of retinal with one or more retinol esters, or a combination of two or more retinol esters.

It is preferable that the aqueous pharmaceutical composition of the present invention contains one or more retinol esters. Even more preferably, the aqueous pharmaceutical composition of the present invention contains one retinol ester.

The retinol ester is not particularly limited and may be any pharmaceutically acceptable ester of retinol. Preferably, the retinol ester is retinol esterified with a carboxylic acid R—COOH, wherein R is $C_{1-25}$ alkyl or $C_{2-25}$ alkenyl, wherein said alkyl and said alkenyl are each optionally substituted with one or more (e.g., one, two or three) hydroxy groups (—OH). Said alkyl is preferably a $C_{1-20}$ alkyl, more preferably a $C_{1-15}$ alkyl, even more preferably a linear $C_{1-15}$ alkyl, and yet even more preferably a group —$(CH_2)_{0-14}$—$CH_3$ (such as, e.g., —$CH_3$, $CH_2$—$CH_3$, —$(CH_2)_2$—$CH_3$, —$(CH_2)_4$—$CH_3$, —$(CH_2)_6$—$CH_3$, —$(CH_2)_8$—$CH_3$, —$(CH_2)_{10}$—$CH_3$, —$(CH_2)_{12}$—$CH_3$, or —$(CH_2)_{15}$—$CH_3$). Said alkenyl is preferably a $C_{2-20}$ alkenyl, more preferably a $C_{2-15}$ alkenyl, and even more preferably a linear $C_{2-15}$ alkenyl (such as, e.g., —$CH_3$, —$CH$=$CH$—$CH_3$). It is preferred that said alkyl or said alkenyl is not substituted with any hydroxy groups. It is furthermore preferred that the group R is an alkyl (as described above).

Accordingly, the retinol ester is preferably retinol esterified with a carboxylic acid R—COOH, wherein R is $C_{1-25}$ alkyl, more preferably wherein R is $C_{1-15}$ alkyl, and even more preferably wherein R is —$(CH_2)_{0-14}$—$CH_3$ (e.g., —$CH_3$, —$CH_2$—$CH_3$, or —$(CH_2)_{15}$—$CH_3$).

It is particularly preferred that the aqueous pharmaceutical composition of the present invention comprises a pharmaceutically acceptable retinol ester which is selected from retinol acetate, retinol propionate and retinol palmitate. Even more preferably, the aqueous pharmaceutical composition comprises retinol palmitate.

The retinol or pharmaceutically acceptable ester thereof is preferably contained in the aqueous pharmaceutical composition of the present invention in an amount of about 0.05 to about 5 wt.-%, preferably about 0.25 to about 3.5 wt.-%, more preferably about 0.5 to about 2.5 wt.-%, even more preferably about 1 to about 2 wt.-%, even more preferably about 1.25 to about 1.75 wt.-%, of the retinol or pharmaceutically acceptable ester thereof, expressed as the mass of retinol, based on the total weight (mass) of the aqueous pharmaceutical composition.

In other words, the retinol or pharmaceutically acceptable ester thereof is preferably contained in the aqueous pharmaceutical composition of the present invention in an amount of about 10 000 to about 200 000 IU (international units), expressed as retinol, per 1 ml; more preferably in an amount of about 50 000 IU, expressed as retinol, per 1 ml.

The One or More Polyethylene Glycol Esters of Hydroxystearic Acid

The aqueous pharmaceutical composition of the present invention contains one or more polyethylene glycol esters of hydroxystearic acid.

Preferably, the one or more polyethylene glycol esters of hydroxystearic acid are each independently a monoester of 12-hydroxystearic acid with polyethylene glycol. The polyethylene glycol is preferably a polyethylene glycol having from about 10 to about 20 ethylene glycol repeating units.

More preferably, the polyethylene glycol ester of hydroxystearic acid is macrogol-15-hydroxystearate, which is 12-hydroxystearic acid polyoxyethylated at the acid functionality with 15 polyoxyethylene repeating units. Macrogol-15-hydroxysterate is a non-ionic solubilizer and emulsifying agent composed of polyglycol mono- and di-esters of 12-hydroxystearic acid (lipophilic part) and about 30 wt-% of free polyethylene glycol (hydrophilic part), and is available with the CAS No. 70142-34-6. Macrogol-15-hydroxystearate is commercially available from BASF as "Solutol HS 15" (NPTL25). It has been found that macrogol-15-hydroxysterate is particularly suitable for the parenteral administration of the aqueous pharmaceutical composition of the invention. Its histamine release is comparable with that of saline which facilitates the use in immune-compromised, vulnerable patients.

The one or more polyethylene glycol esters of hydroxystearic acid is/are preferably contained in the aqueous pharmaceutical composition of the present invention in an amount of about 0.1 to about 50 wt-%, preferably about 2 to about 30 wt.-%, more preferably about 3 to about 25 wt.-%, even more preferably about 5 to about 20 wt.-%, and yet even more preferably about 10 to about 15 wt.-%, based on the total weight of the aqueous pharmaceutical composition. The One or More Pharmaceutically Acceptable Excipients The aqueous pharmaceutical composition according to the invention contains water as solvent. The water in the aqueous pharmaceutical composition is preferably water for injection (e.g., as defined in the European Pharmacopoeia (Ph. Eur.), 8th Edition as of Jul. 1, 2015, including supplement 8.6). Water for injection (WFI) can be prepared using techniques known in the art, e.g., by distillation or by membrane technologies (such as reverse osmosis or ultrafiltration), as described, e.g., in Felton LA (ed.), Remington: Essentials of Pharmaceutics, Pharmaceutical Press, 2013. Moreover, the aqueous pharmaceutical composition according to the present invention is preferably an aqueous solution.

The aqueous pharmaceutical composition of the present invention may, in principle, contain any pharmaceutically acceptable type and amount of excipients.

In order to stabilize the retinol or pharmaceutically acceptable ester thereof, in particular against degradation by oxygen, the aqueous pharmaceutical composition of the present invention preferably contains at least one antioxidant, such as, e.g., ascorbic acid (or a pharmaceutically acceptable salt thereof), citric acid (or a pharmaceutically acceptable salt thereof) and/or phosphoric acid (or a pharmaceutically acceptable salt thereof). It is preferred that the aqueous pharmaceutical composition comprises ascorbic acid or a pharmaceutically acceptable salt thereof, optionally in combination with citric acid (or a pharmaceutically acceptable salt thereof) and/or phosphoric acid (or a pharmaceutically acceptable salt thereof).

As explained above, the aqueous pharmaceutical composition of the present invention preferably contains ascorbic acid or a pharmaceutically acceptable salt thereof. Pharmaceutically acceptable salts of ascorbic acid may be formed, e.g., as a salt of the ascorbate anion with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Preferred pharmaceutically acceptable salts of ascorbic acid include, in particular, sodium ascorbate, potassium ascorbate, or calcium ascorbate. More preferably, the pharmaceutically acceptable salt of ascorbic acid is sodium ascorbate or calcium ascorbate.

It is preferred that the aqueous pharmaceutical composition of the present invention comprises ascorbic acid or a pharmaceutically acceptable salt thereof in an amount of about 2 mg/ml to about 50 mg/ml, more preferably in an amount of about 5 mg/ml to about 20 mg/ml, even more preferably in an amount of about 8 mg/ml to about 15 mg/ml, and yet even more preferably in an amount of about 10 mg/ml, expressed in terms of the amount of ascorbic acid.

The aqueous pharmaceutical composition of the present invention may also contain citric acid or a pharmaceutically acceptable salt thereof. Pharmaceutically acceptable salts of citric acid may be formed, e.g., as a salt of the citrate anion with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Preferred pharmaceutically acceptable salts of citric acid include, in particular, sodium citrate, potassium citrate, or calcium citrate. More preferably, the pharmaceutically acceptable salt of citric acid is sodium citrate or calcium citrate.

If the aqueous pharmaceutical composition of the present invention comprises citric acid or a pharmaceutically acceptable salt thereof, it is preferred that said citric acid or the pharmaceutically acceptable salt thereof is present in an amount of about 2 mg/ml to about 50 mg/ml, more preferably in an amount of about 5 mg/ml to about 20 mg/ml, even more preferably in an amount of about 8 mg/ml to about 15 mg/ml, and yet even more preferably in an amount of about 10 mg/ml, expressed in terms of the amount of citric acid.

Moreover, the aqueous pharmaceutical composition of the present invention may contain phosphoric acid or a pharmaceutically acceptable salt thereof. Pharmaceutically acceptable salts of phosphoric acid may be formed, e.g., as a salt of the phosphate anion with a physiologically acceptable cation. Exemplary base addition salts comprise, for example: alkali metal salts such as sodium or potassium salts; alkaline earth metal salts such as calcium or magnesium salts; zinc salts; ammonium salts; quaternary ammonium salts such as tetramethylammonium salts, tetraethylammonium salts, benzyltrimethylammnonium salts, benzyltriethylammonium salts, benzyltributylammonium salts, methyltrioctylammonium salts or tetrabutylammonium salts; and basic amino acid salts such as arginine salts, lysine salts, or histidine salts. The salts may be dihydrogen phosphate salts, hydrogen phosphate salts or phosphate salts. Preferred pharmaceutically acceptable salts of phosphoric acid include, in particular, trisodium phosphate, disodium hydrogenphosphate, monosodium dihydrogen phosphate, tripotassium phosphate, dipotassium hydrogenphosphate, or monopotassium dihydrogen phosphate. More preferably, the pharmaceutically acceptable salt of phosphoric acid is disodium hydrogenphosphate or dipotassium hydrogenphosphate. If the aqueous pharmaceutical composition of the present invention comprises the phosphoric acid or a pharmaceutically acceptable salt thereof, it is preferred that said phosphoric acid or a pharmaceutically acceptable salt thereof is present in an amount of about 1 mM to about 50 mM, more preferably in an amount of about 2 mM to about 25 mM, even more preferably in an amount of about 5 mM to about 15 mM, and yet even more preferably in an amount of about 10 mM.

In addition, the aqueous pharmaceutical composition of the present invention preferably contains one or more selected from α-tocopherol, β-tocopherol, γ-tocopherol, δ-tocopherol and esters of any one of α-tocopherol, β-tocopherol, γ-tocopherol and δ-tocopherol. The esters and preferred esters are as defined above with respect to the esters of retinal. The tocopherol or ester thereof is advantageous as it allows to prevent degradation of the retinol or ester thereof by light and oxidation. The amount of the respective tocopherol or tocopherol ester is typically less than about 20 mol-%, preferably less than about 10 mol-%, more preferably less than about 5 mol-%, even more preferably less than about 2 mol-%, still more preferably less than about 1 mol-%, relative to the amount of the retinol or ester thereof. The amount of the respective tocopherol or tocopherol ester is preferably more than about 0.001 mol-%, more preferably more than about 0.01 mol-%, even more preferably more than about 0.05 mol-%, still more preferably more than about 0.1 mol-%.

In other words, the ratio of the retinol or ester thereof, expressed as the mass of retinol, to the one or more selected from α-tocopherol, β-tocopherol, γ-tocopherol, δ-tocopherol and esters of any one of α-tocopherol, β-tocopherol, γ-tocopherol and δ-tocopherol is preferably more than about 10:1, about 25:1, about 50:1, about 80:1 or about 90:1 by mass. It is furthermore preferred that the composition comprises a ratio of the retinol or pharmaceutically acceptable ester thereof, expressed as the mass of retinol, to the one or more selected from α-tocopherol, β-tocopherol, γ-tocopherol, δ-tocopherol and esters of any one of α-tocopherol, β-tocopherol, γ-tocopherol and δ-tocopherol of less than about 1000:1, about 800:1, about 400:1, about 200:1 or about 150:1 by mass.

Undesirable Excipients

Prior art vitamin A compositions for intramuscular administration typically solubilize vitamin A using solubilization agents such as polysorbates (e.g. polysorbate 80), polyoxypropylene block copolymers, polyoxyethylen/polyoxypropylene but also polyoxyethylenated hydrogenated castor oil 40 (Kolliphor RH 40), and Kolliphor RH 60 (NPTL 11, NPTL 12, NPLT14)

For example, the commercial vitamin A preparation "Aquasol-A" contains polysorbate 80 as an excipient (NPTL14; NPTL27). Polysorbate 80 as an excipient has led to fatalities in neonates after parenteral administration (NPTL15). The use of drug products containing polysorbate 80 as an excipient are therefore very restricted in infants. Polysorbate 80 is known to be a trigger of histamine leading to anaphylaxia (NPTL16, NPTL 17, NPTL 23). Anaphylactic shock and death have been reported in cases where the intravenous route was used (NPTL16, NPTL 17, NPTL23).

Other products containing vitamin A as a parenteral single vitamin A product are or have been on the market (NPTL11, NPTL12, NPTL14) but are equally unsuitable for premature infants. For example, Vitamin A Nepalm contains polyoxyethylenated hydrogenated castor oil 40, which may lead to anaphylaxia (NPTL11), and benzyl alcohol, which may lead to fatal toxic syndrome in premature infants (NPTL16, NPTL17).

The aqueous pharmaceutical composition of the present invention should be free of any excipients or other compounds that are potentially harmful to infants. Thus, the aqueous pharmaceutical composition is preferably essentially free of (and is more preferably free of) benzalkonium chloride, benzethonium chloride, benzyl alcohol, chlorobutanol, cresol, myristyl gamma-picolinium chloride, methylparaben, propylparaben, phenol, 2-phenoxyethanol, phenyl mercuric nitrate, thimerosal, propylene glycol, ethanol, parahydroxybenzoates, sodium benzoate, benzoic acid, copolymers of polyoxyethylene and polyoxypropylene, polysorbates, polyoxyethylenated hydrogenated castor oil, and sorbitol.

Accordingly, it is preferable that the aqueous pharmaceutical composition comprises less than about 0.0005 mg/ml, preferably less than about 0.0001 mg/ml, based on the volume of the composition, of each of the following substances: propylene glycol, ethanol, parahydroxybenzoates, benzoic acid and salts thereof, copolymers of polyoxyethylene and polyoxypropylene, polysorbates, polyoxyethylenated hydrogenated castor oil, and sorbitol.

Furthermore, it is preferable that the aqueous pharmaceutical composition comprises less than about 0.0005 mg/ml, preferably less than about 0.0001 mg/ml, based on the volume of the composition, of each of the following substances: benzalkonium chloride, benzethonium chloride, benzyl alcohol, chlorobutanol, cresol, myristyl gamma-picolinium chloride, methylparaben, propylparaben, phenol, 2-phenoxyethanol, phenyl mercuric nitrate, and thimerosal.

Antimicrobial preservatives have a high potential for undesirable side effects, particularly in very sensitive patients, such as newborns. The aqueous pharmaceutical composition of the present invention is thus preferably essentially free of (or, more preferably, is free of) antimicrobial preservatives.

Furthermore, it is preferred that the aqueous pharmaceutical composition of the present invention contains one or more of the following substances (more preferably: any/all of the following substances) at most in an amount up to about the maximum limit specified in the following table; most preferably, the composition is free of these substances:

| upper limit (in mg/ml) | preferred | more preferred | even more preferred |
|---|---|---|---|
| benzalkonium chloride | 0.01 | 0.002 | 0.0004 |
| benzethonium chloride | 0.005 | 0.001 | 0.0002 |
| benzyl alcohol | 0.375 | 0.075 | 0.015 |
| chlorobutanol | 0.125 | 0.025 | 0.005 |
| cresol | 0.05 | 0.01 | 0.002 |
| myristyl gamma-picolinium chloride | 0.01 | 0.002 | 0.0004 |
| methylparaben | 0.025 | 0.005 | 0.001 |
| propylparaben | 0.0025 | 0.0005 | 0.0001 |
| phenol | 0.075 | 0.015 | 0.003 |
| 2-phenoxyethanol | 0.25 | 0.05 | 0.01 |
| phenyl mercuric nitrate | 0.0005 | 0.0001 | 0.00002 |
| thimerosal | 0.0015 | 0.0003 | 0.00006 |

The Micelles

In the aqueous pharmaceutical composition of the present invention, the retinol or the pharmaceutically acceptable ester thereof and the one or more polyethylene glycol esters of hydroxystearic acid are present as micelles having a mean particle size of about 100 nm or less.

Micelles are well-known in the art and are typically aggregates of amphiphilic molecules, which are usually dispersed in a liquid. Generally, micelles are approximately spherical in shape. The shape and size of a micelle can be affected by choosing constituent molecules having an appropriate molecular geometry, and by adjusting solution conditions such as the concentration of the constituent amphiphilic molecules, temperature, pH, and/or ionic strength.

Preferably, in the aqueous pharmaceutical composition of present invention, the one or more polyethylene glycol esters of hydroxystearic acid aggregate to form micelles, while the retinol (or the pharmaceutically acceptable ester thereof) is present inside the micelles. The excipients and any further components of the composition may be present within or outside the micelles (or both), typically depending on the hydrophilicity of these excipients or further components.

The size of micelles can be determined using methods known in the art. Preferably, the micelle size is to be determined using a laser diffraction particle size analyser such as, e.g., LS 13 320 by Beckman Coulter. As used herein, the mean particle size preferably refers to the volume mean particle diameter (e.g., as determined by laser diffraction) or the D50 particle diameter (which can be calculated, e.g., using software such as the Horiba laser diffraction software package which is available, e.g., with an LA-960 Horiba laser diffraction apparatus); more preferably, it refers to the volume mean particle diameter.

It has surprisingly been found that the micelles in the compositions of the present invention are particularly insensitive to external mechanical, thermodynamical or physical influences and forces, such as shaking, heating, cooling, diluting and exerting pressure.

Further Properties of the Composition

The aqueous pharmaceutical composition of the present invention has a pH in the range of about 5.5 to about 7.5, preferably a pH of about 6.0 to about 7.0. The pH of the composition of the present invention can be adjusted, e.g., by adding a sufficient amount of an acid or a base. Acids and bases can be added on an "as needed" basis in order to achieve the desired pH. For example, if the pH is greater than the desired pH, an acid can be used to lower the pH to the desired value. Suitable acids include, but are not limited to, any one of hydrochloric acid, phosphoric acid, citric acid, ascorbic acid, acetic acid and sulfuric acid. In particular, hydrochloric acid may be used to adjust the pH. Moreover, if the pH is less than the desired pH, a base can be used to raise the pH to the desired value. Suitable bases include, but are not limited to, any one of sodium hydroxide, potassium hydroxide, calcium hydroxide, sodium carbonate, sodium citrate, sodium acetate, and magnesium hydroxide.

In the context of the present invention, it has surprisingly been found that the aqueous pharmaceutical composition provided herein can be diluted, e.g., with 0.9% sodium chloride solution in water or with 5% dextrose solution in water in various concentrations, and is pharmaceutically stable without disintegration during at least about 24 hours. For example, the composition of the present invention is dilutable with 0.9% sodium chloride solution in water in a ratio of about 1:1, about 1:4, about 1:9, about 1:99, expressed as the volume ratio of the composition of the present invention to the 0.9% sodium chloride solution in water. Similarly, the composition of the present invention is dilutable with 5% dextrose solution in water in a ratio of about 1:1, about 1:4, about 1:9, about 1:99, expressed as the volume ratio of the composition of the present invention to the 5% dextrose solution in water.

It has furthermore been found that the aqueous pharmaceutical composition of the present invention, in particular when containing a combination of ascorbic acid and citric acid, exhibits a high pharmaceutical stability of more than about 12 months if stored at about 2 to about 8° C.

It is preferred that the aqueous pharmaceutical composition is isotonic with respect to human blood plasma. In particular, it is preferred that the aqueous pharmaceutical composition has an osmolality of about 100 mOsm/kg to about 600 mOsm/kg, more preferably an osmolality of about 200 mOsm/kg to about 500 mOsm/kg, even more preferably an osmolality of about 300 mOsm/kg to about 400 mOsm/ kg, even more preferably an osmolality of about 280 mOsm/kg to about 305 mOsm/kg, yet even more preferably an osmolality of about 290 mOsm/kg to about 300 mOsm/kg, and still more preferably an osmolality of about 296 mOsm/kg. Moreover, the aqueous pharmaceutical composition is preferably rendered isotonic (e.g., to any of the aforementioned osmolality ranges or values) using sodium chloride. The aqueous pharmaceutical composition having an osmolality in the aforementioned preferred ranges is advantageous as it avoids any risk of hemolysis and of crenation/shriveling of blood cells, particularly in the vulnerable population of preterm infants. Thus, while hypoosmolality may lead to hemolysis, hyperosmolality may lead to local discomfort and pain and may result in crenation (shriveling) of blood cells.

The aqueous pharmaceutical composition of the present invention is preferably sterilized by filtration, i.e. is sterile-filtered. Filtration involves the use of filter material having pores small enough to retain micro-organisms. The micro-organisms are retained because of the small size of the filter pores and partly by adsorption on the walls of pores while passing through the filter. Typical filters suitable for this purpose exhibit, e.g., a pore size of about 0.22 μm and are preferably made of polyvinylidene difluoride (PVDF), polyethersulfone (PES) or nylon. In particular, filters such as Fluorodyne® II-Filter, Supor® Filter (PES), Ultipor Nylon Filter, which are available from Pall GmbH, Germany, may be used.

Furthermore, the aqueous pharmaceutical composition of the present invention is preferably clear. Accordingly, the composition preferably has a turbidity, as measured in accordance with ISO 7027, of about 150 NTU or less, preferably about 100 NTU or less, more preferably about 50 NTU or less, and even more preferably about 30 NTU or less.

The aqueous pharmaceutical composition may comprise the retinol or the pharmaceutically acceptable ester thereof as the sole active agent, particularly as the sole active agent that is therapeutically effective against the vitamin A deficiency or the vitamin A deficiency-associated disease to be treated or prevented. Accordingly, the aqueous pharmaceutical composition may be free of any other therapeutic agents against vitamin A deficiency or a vitamin A deficiency-associated disease. Alternatively, however, the aqueous pharmaceutical composition may also comprise, in addition to the retinol or the pharmaceutically acceptable ester thereof, one or more further therapeutic agents against vitamin A deficiency or a vitamin A deficiency-associated disease.

Dosage Forms

The aqueous pharmaceutical composition of the present invention is preferably provided in a unit dose container, preferably an ampoule, vial or syringe, wherein the unit dose container is preferably a single unit dose container.

The unit dose container typically contains less than about 8000 μg, preferably less than about 6000 μg, more preferably less than about 5000 μg, and even more preferably less than about 4000 μg of the retinol or the pharmaceutically acceptable ester thereof, expressed as the mass of retinol, per unit dose.

Moreover, the unit dose container typically contains less than about 2 ml, preferably less than about 1 ml, and more preferably less than about 0.5 ml of the aqueous pharmaceutical composition. The unit dose container typically contains more than the amount of the aqueous pharmaceutical composition needed for the intended treatment, in particular in the case where the unit does container is an ampoule. For example, in order to facilitate application by injection, the unit dose container may contain about 0.5 ml of the composition, albeit only about 0.1 ml thereof are to be used in the treatment.

The aqueous pharmaceutical composition of the present invention can suitably be provided in the form of a secondary packaging containing 12 primary packages each containing less than about 2 ml, preferably less than about 1 ml, or more preferably less than about 0.5 ml of the aqueous pharmaceutical composition of the present invention. This is particularly practical for the use as a paediatric medicament.

The aqueous pharmaceutical composition preferably contains the retinol or the pharmaceutically acceptable ester thereof in a concentration of about 50 000 IU/ml. The amount of the aqueous pharmaceutical composition to be administered as a single-dose is preferably about 0.1 ml, containing about 5000 IU of retinol or a pharmaceutically acceptable ester thereof.

Subjects to be Treated

The subject (or patient) to be treated in accordance with the present invention may be an animal, particularly a mammal (e.g., a non-human mammal, such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig), and is preferably a human (e.g., a male human or a female human).

The subject (or patient) to be treated with the aqueous pharmaceutical composition of the present invention is preferably a human child, which is understood to be any human at the age of less than about 18 years. The human child is preferably a human infant, i.e. a human at the age of less than about 1 year.

The subject/patient to be treated is more preferably a neonate human infant, i.e. a human at the age of less than about 1 month after birth. Even more preferably, the subject to be treated is a preterm human infant, which is a human infant born at fewer than about 37 weeks gestational age, preferably fewer than about 34 weeks gestational age, or more preferably fewer than about 32 weeks gestational age.

The human infant (or neonate human infant) to be treated in accordance with the present invention preferably has a birth weight of less than about 4200 g, more preferably of less than about 2500 g, even more preferably of less than about 2000 g, and yet even more preferably of less than about 1500 g.

The preterm human infant is preferably a human infant no older than about 15 weeks, more preferably no older than about 12 weeks, even more preferably no older than about 10 weeks, yet even more preferably no older than about 7 weeks, and still more preferably no older than about 4 weeks past birth.

Routes of Administration

The aqueous pharmaceutical composition according to the present invention is preferably administered parenterally. More preferably, the aqueous pharmaceutical composition is to be administered intravenously, intramuscularly, subcutaneously, intra-arterially, intraocularly, intravitreally or intraosseously. Even more preferably, the aqueous pharmaceutical composition is to be administered intravenously, intramuscularly, subcutaneously or intra-arterially. Still more preferably, the aqueous pharmaceutical composition is to be administered intravenously or intramuscularly.

Venous access via a peripheral vein, umbilical vein or central catheter is normally established in preterm infants in the neonatal intensive care. For this route of administration, small amounts of high doses of vitamin A are usually diluted in order to allow for exact dosing over time, particularly for either slow direct intravenous administration or via a syringe pump. Especially for this route of administration, the beneficial property of the aqueous pharmaceutical composition according to the present invention of being easily dilutable is of particular importance.

Parenteral administration is particularly important in very preterm infants as retinol and its pharmaceutically acceptable esters are often not sufficiently absorbed through the gastrointestinal tract. Subsequent transfer of orally ingested retinol from enterocytes into the lymphatic system is dependent upon cellular retinol-binding protein type 2 (CRBP II). Reduced availability of CRBP II combined with an immature gastrointestinal tract explain the lack of efficacy of previously known oral dosage forms of vitamin A in many preterm infants (NPTL18; NPTL19, NPTL24).

The aqueous pharmaceutical composition of the present invention is particularly advantageous in that it allows for both intravenous (IV) and intramuscular (IM) administration. The reason for the interest in both routes (IV/IM) within the parenteral administration is that very low birth weight infants (VLBW infants) have a peripherally or centrally inserted catheters from day one, which is usually removed after 10 days to 14 days. Very often they have no longer a venous access at a later stage, which subsequently requires intramuscular administration. Likewise, more mature VLBW babies (birth weight of 1000 to 1500 g) might not have a venous access at all, which might require intramuscular administration.

Thus, the aqueous pharmaceutical composition of the present invention allowing both IV and IM administration is highly beneficial as it can diminish pain and the risk of infection.

Dosage Regimens

Typically, a physician will determine the actual dosage which will be most suitable for an individual subject. The specific dose level and frequency of dosage for any particular individual subject may be varied and will depend upon a variety of factors including the activity of the specific form of retinol employed, the metabolic stability and length of action of this specific form of retinol, the age, body weight, general health, sex, diet, mode and time of administration, rate of excretion, drug combination, the severity of the particular condition, and the individual subject undergoing therapy. It is to be understood that the aqueous pharmaceutical composition according to the invention is to be administered to a subject in a therapeutically effective amount (i.e., a therapeutically effective amount with respect to the retinol or the pharmaceutically acceptable ester thereof comprised in the aqueous pharmaceutical composition).

The aqueous pharmaceutical composition according to the present invention is preferably administered as about 1 to about 30 doses over a period of about 1 to about 7 weeks, wherein each dose contains about 800 µg to about 4000 µg of the retinol or the pharmaceutically acceptable ester thereof, expressed as the mass of retinol.

For example, the aqueous pharmaceutical composition according to the present invention may be administered as about 3 to about 21 doses over a period of about 1 to about 7 weeks, wherein each dose contains about 1200 to about 3600 µg of the retinol or the pharmaceutically acceptable ester thereof, expressed as the mass of retinol.

When the aqueous pharmaceutical composition of the present invention is used for prophylaxis (as a preventative measure), the treatment is typically administered over about 4 weeks. The administration may occur about 3 times a week, e.g. Monday, Wednesday, and Friday. The amount to be administered may be about 0.1 ml of the composition containing 5000 IU.

Therapeutic Applications

The aqueous pharmaceutical composition according to the present invention can be used in the treatment or prevention of vitamin A deficiency or in the treatment or prevention of any vitamin A deficiency-associated disease, in particular any disease where the supply of vitamin A has been described to be beneficial either to prevent or treat the disease. This also includes any disease that may be acquired due to, or as a result of, a deficiency in vitamin A.

Examples of vitamin A deficiency-associated diseases that can be treated or prevented in accordance with the present invention include, but are not limited to, bronchopulmonary dysplasia, retinopathy of prematurity, liver disease with cholestasis, biliary atresia, diseases associated with liver transplantation, primary biliary cirrhosis, conjunctival xerosis, Bitot's spot, corneal xerosis, corneal ulceration and xerosis, keratomalacia, night blindness, dark adaptation, xerophthalmic scars of cornea, ocular manifestations, xerophthalmia nos, measles, or kwashiorkor. The ICD 10 codes for these diseases include P27.1, H35.1, K71.0, Q44.2, Y83, K74.3, E50.0, E50.1, E50.2, E50.3, E50.4, E50.5, E50.6, E50.7, B05 and E40.

Preferably, the vitamin A deficiency-associated disease to be treated or prevented is retinopathy of prematurity (ROP) or is bronchopulmonary dysplasia (BPD).

Definitions

The following definitions apply throughout the present specification and the claims, unless specifically indicated otherwise.

In the present invention, the amounts of the retinol or pharmaceutically acceptable ester thereof are expressed in terms of the mass of retinol. Thus, when a pharmaceutically acceptable ester is used, the equivalent retinol mass is obtainable by dividing the mass of the pharmaceutically acceptable ester by the molar mass thereof and multiplying the resulting number by the molar mass of retinol.

Accordingly, the amounts of the retinol or pharmaceutically acceptable ester thereof, as referred to in the present invention, can also be expressed using the unit RAE (retinol activity equivalents). 1 mg of retinol corresponds to 1 RAE. 1 RAE corresponds to about 1.147 mg retinyl acetate or about 1.833 mg retinyl palmitate. 1 mg of retinol may also be expressed as 3333 IU (international units) of retinol.

The term "hydrocarbon group" refers to a group consisting of carbon atoms and hydrogen atoms.

The term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Examples of alkyl groups include methyl, ethyl, propyl (e.g., n-propyl or isopropyl), or butyl (e.g., n-butyl, isobutyl, sec-butyl, or tert-butyl).

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Examples of alkenyl groups include ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl).

As used herein, the term "paediatric" (e.g., as used in "paediatric medicament") refers to the treatment of any subject/patient who is not yet fully grown (or is below the age of majority), including for example a human being at an age of less than about 18 years, particularly a human at an age of less than about 10 years, more preferably a human at an age of less than about 5 years, and a even more preferably a human at an age of less than about 1 year.

The term "active pharmaceutical ingredient" or API as used herein refers to a substance used in a finished pharmaceutical product (FPP), intended to furnish pharmacological activity or to otherwise have direct effect in the diagnosis, cure, mitigation, treatment or prevention of disease, or to have direct effect in restoring, correcting or modifying physiological functions in human beings.

The term "treatment" of a disorder or disease as used herein is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease) and palliative treatment (including symptomatic relief).

The term "prevention" of a disorder or disease as used herein is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of the aqueous pharmaceutical composition of the present invention before any clinical and/or pathological symptoms are diagnosed or determined or can be diagnosed or determined by the attending physician.

The term "about" preferably refers to ±10% of the indicated numerical value, more preferably to ±5% of the indicated numerical value, and in particular to the exact numerical value indicated. If the term "about" is used in connection with the endpoints of a range, it preferably refers to the range from the lower endpoint −10% of its indicated numerical value to the upper endpoint +10% of its indicated numerical value, more preferably to the range from of the lower endpoint −5% to the upper endpoint +5%, and even more preferably to the range defined by the exact numerical values of the lower endpoint and the upper endpoint. If the term "about" is used in connection with the endpoint of an open-ended range, it preferably refers to the corresponding range starting from the lower endpoint −10% or from the upper endpoint +10%, more preferably to the range starting from the lower endpoint −5% or from the upper endpoint +5%, and even more preferably to the open-ended range defined by the exact numerical value of the corresponding endpoint.

The terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

The term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

As used herein, unless explicitly indicated otherwise or contradicted by context, the terms "a", "an" and "the" are used interchangeably with "one or more" and "at least one". Thus, for example, a composition comprising "a" retinol ester can be interpreted as referring to a composition comprising "one or more" retinol esters.

Unless specifically indicated otherwise, all properties and parameters referred to herein (including, e.g., any amounts/concentrations indicated in "mg/ml", in "% (w/v)" or in "% (v/v)", and any pH values) are preferably to be determined at standard ambient temperature and pressure conditions, particularly at a temperature of 25° C. (298.15 K) and at an absolute pressure of 1 atm (101.325 kPa).

Moreover, unless indicated otherwise, any reference to an industry standard, a pharmacopeia, or a manufacturer's manual refers to the corresponding latest (i.e., most recent) version that was available on Oct. 1, 2018.

It is to be understood that the present invention specifically relates to each and every combination of features and embodiments described herein, including any combination of general and/or preferred features/embodiments.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The reference in this specification to any prior publication (or information derived therefrom) is not and should not be taken as an acknowledgment or admission or any form of suggestion that the corresponding prior publication (or the information derived therefrom) forms part of the common general knowledge in the technical field to which the present specification relates.

The present invention particularly relates to the following items:

1. An aqueous pharmaceutical composition for use as a paediatric medicament in the treatment or prevention of vitamin A deficiency or a vitamin A deficiency-associated disease, wherein the composition comprises:

retinol or a pharmaceutically acceptable ester thereof, one or more polyethylene glycol esters of hydroxystearic acid, and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less; and wherein the composition has an osmolality of about 100 to about 600 mOsm/kg.

2. The aqueous pharmaceutical composition for use according to item 1, wherein the composition is a transparent aqueous pharmaceutical composition.

3. The aqueous pharmaceutical composition for use according to item 1 or 2, wherein the composition comprises a pharmaceutically acceptable retinol ester which is retinol esterified with a carboxylic acid R—COOH, wherein R is $C_{1-25}$ alkyl or $C_{2-25}$ alkenyl, wherein said alkyl and said alkenyl are each optionally substituted with one or more hydroxy groups.

4. The aqueous pharmaceutical composition for use according to any one of items 1 to 3, wherein the composition comprises a pharmaceutically acceptable retinol ester which is selected from retinol acetate, retinal propionate and retinol palmitate.

5. The aqueous pharmaceutical composition for use according to any one of items 1 to 4, wherein the one or more polyethylene glycol esters of hydroxystearic acid are each independently a monoester of 12-hydroxystearic acid with polyethylene glycol having from about 10 to about 20 ethylene glycol repeating units.

6. The aqueous pharmaceutical composition for use according to any one of items 1 to 5, wherein the polyethylene glycol ester of hydroxystearic acid is macrogol-15-hydroxystearate.

7. The aqueous pharmaceutical composition for use according to any one of items 1 to 6, wherein the composition comprises one or more selected from α-tocopherol, β-tocopherol, γ-tocopherol, δ-tocopherol and esters of any one of α-tocopherol, β-tocopherol, γ-tocopherol and δ-tocopherol.

8. The aqueous pharmaceutical composition for use according to item 7, wherein the composition comprises a ratio of the retinol or ester thereof, expressed as the mass of retinol, to the one or more selected from α-tocopherol, β-tocopherol, γ-tocopherol, δ-tocopherol and esters of any one of α-tocopherol, β-tocopherol, γ-tocopherol and δ-tocopherol of more than about 10:1, about 25:1, about 50:1, about 80:1 or about 90:1 by mass.

9. The aqueous pharmaceutical composition for use according to item 7 or 8, wherein the composition comprises a ratio of the retinol or pharmaceutically acceptable ester thereof, expressed as the mass of retinol, to the one or more selected from α-tocopherol, β-tocopherol, γ-tocopherol, δ-tocopherol and esters of any one of α-tocopherol, β-tocopherol, γ-tocopherol and δ-tocopherol of less than about 1000:1, about 800:1, about 400:1, about 200:1 or about 150:1 by mass.

10. The aqueous pharmaceutical composition for use according to any one of items 1 to 9, wherein the composition comprises about 0.05 to about 5 wt.-%, preferably about 0.25 to about 3.5 wt.-%, more preferably about 0.5 to about 2.5 wt.-%, even more preferably about 1 to about 2 wt.-%, even more preferably about 1.25 to about 1.75 wt.-%, of the retinol or pharmaceutically acceptable ester thereof, expressed as the mass of retinol, based on the total weight of the aqueous pharmaceutical composition.

11. The aqueous pharmaceutical composition for use according to any one of items 1 to 10, wherein the composition comprises about 0.1 to about 50 wt.-%, preferably about 2 to about 30 wt.-%, more preferably about 3 to about 25 wt.-%, even more preferably about 5 to about 20 wt.-%, even more preferably about 10 to about 15 wt.-%, of the one or more polyethylene glycol esters of hydroxystearic acid, based on the total weight of the aqueous pharmaceutical composition.

12. The aqueous pharmaceutical composition for use according to any one of items 1 to 11, wherein the composition comprises ascorbic acid or a pharmaceutically acceptable salt thereof, optionally in combination with one or more selected from citric acid or a pharmaceutically acceptable salt thereof, and phosphoric acid or a pharmaceutically acceptable salt thereof.

13. The aqueous pharmaceutical composition for use according to any one of items 1 to 12, wherein the composition comprises less than about 0.0005 mg/ml, preferably less than about 0.0001 mg/ml, of each of propylene glycol, ethanol, parahydroxybenzoates, benzoic acid and salts thereof, copolymers of polyoxyethylene and polyoxypropylene, polysorbates, polyoxyethylenated hydrogenated castor oil, and sorbitol, based on the volume of the aqueous pharmaceutical composition, and wherein the composition is preferably free of the aforementioned substances.

14. The aqueous pharmaceutical composition for use according to any one of items 1 to 13, wherein the composition comprises less than about 0.0005 mg/ml, preferably less than about 0.0001 mg/ml, of each of benzalkonium chloride, benzethonium chloride, benzyl alcohol, chlorobutanol, cresol, myristyl gamma-picolinium chloride, methylparaben, propylparaben, phenol, 2-phenoxyethanol, phenyl mercuric nitrate and thimerosal, based on the volume of the aqueous pharmaceutical composition, and wherein the composition is preferably free of the aforementioned substances.

15. The aqueous pharmaceutical composition for use according to any one of items 1 to 14, wherein the composition is an aqueous solution.

16. The aqueous pharmaceutical composition for use according to any one of items 1 to 15, wherein the composition has an osmolality of about 270 to about 330 mOsm/kg.

17. The aqueous pharmaceutical composition for use according to any one of items 1 to 16, wherein the composition has a turbidity, as measured in accordance with ISO 7027, of about 150 NTU or less, preferably about 100 NTU or less, more preferably about 50 NTU or less, and even more preferably about 30 NTU or less.

18. The aqueous pharmaceutical composition for use according to any one of items 1 to 17, wherein the composition contains about 100 000 IU or less of the retinol or pharmaceutically acceptable ester thereof, expressed as retinol, per 1 ml.

19. The aqueous pharmaceutical composition for use according to any one of items 1 to 18, wherein the composition is provided in a unit dose container, preferably an ampoule, vial or syringe, wherein the unit dose container is preferably a single unit dose container.

20. The aqueous pharmaceutical composition for use according to item 19, wherein the unit dose container contains less than about 8000 μg, preferably less than about 6000 μg, more preferably less than about 5000 μg, even more preferably less than about 4000 μg of the retinol or the pharmaceutically acceptable ester thereof, expressed as the mass of retinol.

21. The aqueous pharmaceutical composition for use according to item 19 or 20, wherein the unit dose container contains less than about 2 ml, preferably less than about 1 ml, and more preferably less than about 0.5 ml of the composition.

22. The aqueous pharmaceutical composition for use according to any one of items 1 to 21, wherein the subject to be treated is a human child.

23. The aqueous pharmaceutical composition for use according to any one of items 1 to 21, wherein the subject to be treated is a human infant.

24. The aqueous pharmaceutical composition for use according to any one of items 1 to 22, wherein the subject to be treated is a neonate human infant, preferably a preterm human infant.

25. The aqueous pharmaceutical composition for use according to any one of items 1 to 24, wherein the vitamin A deficiency-associated disease is retinopathy of prematurity or is bronchopulmonary dysplasia.

26. The aqueous pharmaceutical composition for use according to item 24 or 25, wherein the preterm human infant is a human infant born at fewer than about 37 weeks gestational age, preferably fewer than about 32 weeks gestational age.

27. The aqueous pharmaceutical composition for use according to any one of items 22 to 26, wherein the human infant has a birth weight of less than about 4200 g, preferably less than about 2500 g, more preferably less than about 2000 g, and even more preferably less than about 1500 g.

28. The aqueous pharmaceutical composition for use according to any one of items 24 to 27, wherein the preterm human infant is a human infant no older than about 15 weeks, preferably no older than about 12 weeks, more preferably no older than about 10 weeks, even more preferably no older than about 7 weeks and still more preferably no older than about 4 weeks past birth.

29. The aqueous pharmaceutical composition for use according to any one of items 1 to 28, wherein the composition is to be administered parenterally.

30. The aqueous pharmaceutical composition for use according to any one of items 1 to 29, wherein the composition is to be administered intravenously or intramuscularly.

31. The aqueous pharmaceutical composition for use according to any one of items 1 to 30, wherein the composition is sterile-filtered.

32. The aqueous pharmaceutical composition for use according to any one of items 29 to 31, wherein the composition is to be administered as about 1 to about 30 doses over a period of about 1 to about 7 weeks, wherein each dose contains about 800 μg to about 4000 μg of the retinol or the pharmaceutically acceptable ester thereof, expressed as the mass of retinol.

33. The aqueous pharmaceutical composition for use according to any one of items 29 to 32, wherein the composition is to be administered as about 3 to about 21 doses over a period of about 1 to about 7 weeks, wherein each dose contains about 1200 to about 3600 μg of the retinol or the pharmaceutically acceptable ester thereof, expressed as the mass of retinol.

34. The aqueous pharmaceutical composition for use according to any one of items 29 to 33, wherein the composition is to be administered as about 9 to about 15 doses over a period of about 3 to about 5 weeks, wherein each dose contains about 1500 to about 3300 μg of the retinol or the pharmaceutically acceptable ester thereof, expressed as the mass of retinol.

35. The aqueous pharmaceutical composition for use according to any one of items 29 to 34, wherein the composition is to be administered about 3 times a week.

36. A method of treating or preventing vitamin A deficiency or a vitamin A deficiency-associated disease, the method comprising administering an aqueous pharmaceutical composition to a subject in need thereof, wherein the composition comprises:

retinol or a pharmaceutically acceptable ester thereof, one or more polyethylene glycol esters of hydroxystearic acid, and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less; and wherein the composition has an osmolality of about 100 to about 600 mOsm/kg.

37. The method according to item 36, wherein the composition is a transparent aqueous pharmaceutical composition.

38. The method according to item 36 or 37, wherein the composition comprises a pharmaceutically acceptable retinol ester which is retinol esterified with a carboxylic acid R—COOH, wherein R is $C_{1-25}$ alkyl or $C_{2-25}$ alkenyl, wherein said alkyl and said alkenyl are each optionally substituted with one or more hydroxy groups.

39 The method according to any one of items 36 to 38, wherein the composition comprises a pharmaceutically acceptable retinol ester which is selected from retinol acetate, retinol propionate and retinol palmitate.

40. The method according to any one of items 36 to 39, wherein the one or more polyethylene glycol esters of hydroxystearic acid are each independently a monoester of 12-hydroxystearic acid with polyethylene glycol having from about 10 to about 20 ethylene glycol repeating units.

41. The method according to any one of items 36 to 40, wherein the polyethylene glycol ester of hydroxystearic acid is macrogol-15-hydroxystearate.

42. The method according to any one of items 36 to 41, wherein the composition comprises one or more selected from α-tocopherol, β-tocopherol, γ-tocopherol, δ-tocopherol and esters of any one of α-tocopherol, β-tocopherol, γ-tocopherol and δ-tocopherol.

43. The method according to item 42, wherein the composition comprises a ratio of the retinol or ester thereof, expressed as the mass of retinol, to the one or more selected from α-tocopherol, β-tocopherol, γ-tocopherol, δ-tocopherol and esters of any one of α-tocopherol, β-tocopherol, γ-tocopherol and δ-tocopherol of more than about 10:1, about 25:1, about 50:1, about 80:1 or about 90:1 by mass.

44. The method according to item 42 or 43, wherein the composition comprises a ratio of the retinol or pharmaceutically acceptable ester thereof, expressed as the mass of retinol, to the one or more selected from α-tocopherol, β-tocopherol, γ-tocopherol, δ-tocopherol and esters of any one of α-tocopherol, β-tocopherol, γ-tocopherol and δ-tocopherol of less than about 1000:1, about 800:1, about 400:1, about 200:1 or about 150:1 by mass.

45. The method according to any one of items 36 to 44, wherein the composition comprises about 0.05 to about 5 wt.-%, preferably about 0.25 to about 3.5 wt.-%, more preferably about 0.5 to about 2.5 wt.-%, even more preferably about 1 to about 2 wt.-%, even more preferably about 1.25 to about 1.75 wt.-%, of the retinol or pharmaceutically acceptable ester thereof, expressed as the mass of retinol, based on the total weight of the aqueous pharmaceutical composition.

46. The method according to any one of items 36 to 45, wherein the composition comprises about 0.1 to about 50 wt-%, preferably about 2 to about 30 wt.-%, more preferably about 3 to about 25 wt.-%, even more preferably about 5 to about 20 wt.-%, even more preferably about 10 to about 15 wt.-%, of the one or more polyethylene glycol esters of hydroxystearic acid, based on the total weight of the aqueous pharmaceutical composition.

47. The method according to any one of items 36 to 46, wherein the composition comprises ascorbic acid or a pharmaceutically acceptable salt thereof, optionally in combination with one or more selected from citric acid or a pharmaceutically acceptable salt thereof, and phosphoric acid or a pharmaceutically acceptable salt thereof.

48. The method according to any one of items 36 to 47, wherein the composition comprises less than about 0.0005 mg/ml, preferably less than about 0.0001 mg/ml, of each of propylene glycol, ethanol, parahydroxybenzoates, benzoic acid and salts thereof, copolymers of polyoxyethylene and polyoxypropylene, polysorbates, polyoxyethylenated hydrogenated castor oil, and sorbitol, based on the volume of the aqueous pharmaceutical composition, and wherein the composition is preferably free of the aforementioned substances.

49. The method according to any one of items 36 to 48, wherein the composition comprises less than about 0.0005 mg/ml, preferably less than about 0.0001 mg/ml, of each of benzalkonium chloride, benzethonium chloride, benzyl alcohol, chlorobutanol, cresol, myristyl gamma-picolinium chloride, methylparaben, propylparaben, phenol, 2-phenoxyethanol, phenyl mercuric nitrate and thimerosal, based on the volume of the aqueous pharmaceutical composition, and wherein the composition is preferably free of the aforementioned substances.

50. The method according to any one of items 36 to 49, wherein the composition is an aqueous solution.

51. The method according to any one of items 36 to 50, wherein the composition has an osmolality of about 270 to about 330 mOsm/kg.

52. The method according to any one of items 36 to 51, wherein the composition has a turbidity, as measured in accordance with ISO 7027, of about 150 NTU or less, preferably about 100 NTU or less, more preferably about 50 NTU or less, and even more preferably about 30 NTU or less.

53. The method according to any one of items 36 to 52, wherein the composition contains about 100 000 IU or less of the retinol or pharmaceutically acceptable ester thereof, expressed as retinol, per 1 ml.

54. The method according to any one of items 36 to 53, wherein the composition is provided in a unit dose container, preferably an ampoule, vial or syringe, wherein the unit dose container is preferably a single unit dose container.

55. The method according to item 54, wherein the unit dose container contains less than about 8000 μg, preferably less than about 6000 μg, more preferably less than about 5000 μg, even more preferably less than about 4000 μg of the retinol or the pharmaceutically acceptable ester thereof, expressed as the mass of retinol.

56. The method according to item 54 or 55, wherein the unit dose container contains less than about 2 ml, preferably less than about 1 ml, and more preferably less than about 0.5 ml of the composition.

57. The method according to any one of items 36 to 56, wherein the subject is a human child.

58. The method according to any one of items 36 to 57, wherein the subject is a human infant.

59. The method according to any one of items 36 to 58, wherein the subject is a neonate human infant, preferably a preterm human infant.

60. The method according to any one of items 36 to 59, wherein the vitamin A deficiency-associated disease is retinopathy of prematurity or is bronchopulmonary dysplasia.

61. The method according to item 59 or 60, wherein the preterm human infant is a human infant born at fewer than about 37 weeks gestational age, preferably fewer than about 32 weeks gestational age.

62. The method according to any one of items 58 to 61, wherein the human infant has a birth weight of less than about 4200 g, preferably less than about 2500 g, more preferably less than about 2000 g, and even more preferably less than about 1500 g.

63. The method according to any one of items 59 to 62, wherein the preterm human infant is a human infant no older than about 15 weeks, preferably no older than about 12 weeks, more preferably no older than about 10 weeks, even more preferably no older than about 7 weeks and still more preferably no older than about 4 weeks past birth.

64. The method according to any one of items 36 to 63, wherein the composition is administered parenterally.

65. The method according to any one of items 36 to 64, wherein the composition is administered intravenously or intramuscularly.

66. The method according to any one of items 36 to 65, wherein the composition is sterile-filtered.

67. The method according to any one of items 64 to 66, wherein the composition is administered as about 1 to about 30 doses over a period of about 1 to about 7 weeks, wherein each dose contains about 800 μg to about 4000 μg of the retinol or the pharmaceutically acceptable ester thereof, expressed as the mass of retinol.

68. The method according to any one of items 64 to 67, wherein the composition is administered as about 3 to about 21 doses over a period of about 1 to about 7 weeks, wherein each dose contains about 1200 to about 3600 μg of the retinol or the pharmaceutically acceptable ester thereof, expressed as the mass of retinol.

69. The method according to any one of items 64 to 68, wherein the composition is administered as about 9 to about 15 doses over a period of about 3 to about 5 weeks, wherein each dose contains about 1500 to about 3300 μg of the retinol or the pharmaceutically acceptable ester thereof, expressed as the mass of retinol.

70. The method according to any one of items 64 to 69, wherein the composition is administered about 3 times a week.

In a further embodiment, the present invention provides a pharmaceutical composition comprising (i) retinol or a pharmaceutically acceptable ester thereof, (ii) one or more polyethylene glycol esters of hydroxystearic acid, and (iii) one or more pharmaceutically acceptable excipients, wherein said composition is an aqueous composition. This pharmaceutical composition can be used as a medicament, particularly as a paediatric medicament, e.g., in the treatment or prevention of vitamin A deficiency or a vitamin A deficiency-associated disease. It is preferred that this pharmaceutical composition: (a) has a pH in the range of 5.5 to 7.5; (b) contains the retinol or the pharmaceutically acceptable ester thereof and the one or more polyethylene glycol esters of hydroxystearic acid in the form of micelles having a mean particle size of 100 nm or less; and/or (c) has an osmolality of 100 to 600 mOsm/kg. The further preferred features described in this specification with respect to the aqueous pharmaceutical composition according to the present invention, as well as the general and preferred description of the therapeutic uses/applications of the aqueous pharmaceutical composition of the present invention, likewise apply to the pharmaceutical composition described and provided in this paragraph.

The invention will now be described by reference to the following examples which are merely illustrative and are not to be construed as a limitation of the scope of the present invention.

EXAMPLES

Example 1: Preparation of a Composition of the Present Invention

A composition of the present invention was prepared by first weighing the required amount of macrogol-15-hydroxystearate (12.5 g, obtained from BASF SE—Nutrition & Health, Germany) and retinyl palmitate (3 g, obtained from DSM Nutritional Products Ltd), and adding both into an Erlenmeyer flask under light protection and under inert gas flushing. The flask was put on a heating plate, while being slowly heated to between 55 and 58° C. Stirring using a magnetic stirrer with agitator was initiated once the substances started to melt.

Approximately 95 g of water for injection (containing further excipient(s), where desired) was heated up to between 55 and 58° C. in a further Erlenmeyer flask and slowly added to the Erlenmeyer flask containing the mixed macrogol-15-hydroxystearate and retinyl palmitate up to 100 ml of total volume. The mixture was continuously stirred, and purged with inert gas even during the cooling down phase until room temperature was reached.

The aqueous composition was sterile filtered and then filled into vials, ampoules or syringes while keeping it in an atmosphere of an inert gas. Either argon or nitrogen, or a mixture thereof, was used as the inert gas.

Example 2: In-Use Stability of a Composition of the Present Invention and a Competitor Product in Small Volume Syringes Plastic disposables are lipophilic and thus ingredients with a high lipophilicity such as vitamin A can adhere to the test solution in the medical device simulated in-use stability. For comparison, at $t=180$ the storage was also performed under light-protection (with aluminium foil). For the different time points, relative retinol content was measured. In order to measure the absolute retinol content, the primary packages of the composition of the present invention and the comparator product were opened and the absolute content was determined by HPLC. This was used as a reference point (set as 1) for the measurements after syringe administration ($t=0/t=180$ (light protection/no light protection)).

TABLE 1

The composition according to the present invention (cf. Example 1) and a comparator product - Vitamine A Nepalm (Marketing Authorisation Holder Lexphar SARL, LOT F0020/Exp. 01/2019) were tested according the following test matrix allowing a comparison of in-use stability over time.

| Medical Device/ Test solution | Retention time T [min} | No. of tests | Test solution volume | Nominal IU per diluted test solution | Relative Retinol content (measured by HPLC) |
|---|---|---|---|---|---|
| 1 mL syringe/ inventive composition | $t = 0$ | 10 | $10 \times 0.10$ mL = 1.0 mL | 50.000 IU ($10 \times 5.000$ IU) | 1.00 |
| 1 mL syringe/ Vitamine A Nepalm | $t = 0$ | 10 | $10 \times 0.10$ mL = 1.0 mL | 50.000 IU ($10 \times 5.000$ IU) | 0.78 |
| 1 mL syringe/ inventive composition | $t = 180$ | 10 | $10 \times 0.10$ mL = 1.0 mL | 50.000 IU ($10 \times 5.000$ IU) | 0.96 |
| 1 mL syringe/ Vitamine A Nepalm | $t = 180$ | 10 | $10 \times 0.10$ mL = 1.0 mL | 50.000 IU ($10 \times 5.000$ IU) | 0.76 |
| 1 mL syringe/ inventive composition | $t = 180$ (light protected) | 10 | $10 \times 0.10$ mL = 1.0 mL | 50.000 IU ($10 \times 5.000$ IU) | 1.0 |
| 1 mL syringe/ Vitamine A Nepalm | $t = 180$ (light protected) | 10 | $10 \times 0.10$ mL = 1.0 mL | 50.000 IU ($10 \times 5.000$ IU) | 0.68 | those, and thus not reach the patient to exert a pharmacological effect (NPTL20, NPTL21).

In many hospitals it is common practice to prepare patient specific doses in the hospital pharmacy, e.g. by withdrawing the right amount into syringes allowing a direct administration for the physician/nurse in intensive care. Some products degrade or adsorb during storage in syringes. Therefore, it is important to ensure in-use stability of Vitamin A compounds. It was found that the composition of the present invention is less light sensitive and exhibits less sorption to plastic syringes over time as compared to a competitor product (Vitamine A Nepalm, NPTL11).

Test Description:

Vitamin A is light and oxygen sensitive and also lipophilic. This means that, depending on the formulation, in-use stability mainly influenced by oxidation, light and sorption of Vitamin A to the plastic syringe might impact the dose finally reaching the patient. For this reason, sorption and the impact of time and light of the composition of the present invention compared to a comparator product were tested. Commonly used small volume syringes in intensive care carry a volume equal to or less than 1 ml. For this reason, 1 ml high precision syringes were employed (Single Use Insulin Syringe, Henry Schein 30G, Article Number 9008529).

At any one time, 0.10 ml of the composition of the present invention and 0.10 ml of the comparator product (Vitamine-A Nepalm) were drawn into 1 ml syringes, using a new syringe in each test. This was executed 10 times per test with different retention times (0 to 180 min as well as 180 min with light protection). The time period of the holding time of Corresponding results are also shown in FIG. 1.

As shown in Table 1 and FIG. 1, it has been found that the composition of the present invention did not lose any Vitamin A content over time, particularly if the syringe was light protected for the entire period of 180 min. In contrast, more than 20% of Vitamin A in the comparator product was lost at $t=0$ and between 24% (light protected) to 32% (no light protection) at $t=180$.

It has thus been established that the composition of the present invention is considerably less prone to be either sorbed by the syringe (as seen in the immediate administration) or degraded by light in small volume plastic syringes over time as compared to the competitor product.

The composition of the present invention thus exhibits an advantageous in-use stability.

Example 3: Degradation and Sorption of the Composition of the Invention to Intravenous Infusion Tubing as Commonly Used in Neonatal Intensive Care Lipophilic products such as Vitamin A are generally prone to be sorbed by infusion lines resulting in limited uptake and potential failure of the prevention or treatment of a disease (NPTL 20, NPTL 21).

Thus, intravenous infusion of a composition of the present invention was simulated in a set-up commonly used around the globe in neonatal intensive care. Preterm infants in intensive care have commonly intravenous access, very often through umbilical catheters. In order to hydrate and supply the patient with nutrients and medicaments, specific perfusors (e.g. syringe pump) are attached to the access lines. These supply the patient with solutions such as 5% dextrose or 0.9% sodium chloride at a slow rate. A three-way stop cock is situated between the perfusor and the umbilical catheter allowing administration of small volumes of drugs. After administration of the drug through the stop cock, the drug is slowly pushed through the umbilical venous line by the solution- and thus reaches the patient.

Test Description:

Different intravenous umbilical catheters made of different materials were used (supplier Vygon, 1270.02/PUR, 270.03/PVC, 2184.01/Silicone) in order to test suitability of the composition of the present invention. A perfusor syringe (50 mL) was filled with dilution media (0.9% NaCl) and was used continuously during the test. The infusion rate of the perfusor (Perfusor Secura FT, B. Braun) was set at 5 mL/h, which is a common rate used in preterm infants. Catheters were flushed and primed with 0.9% NaCl before administration. 3 different types of catheters were employed for this test. Per catheter type, 5 catheters were tested (3×5=15 catheters) in order to have sufficient validity.

For each test, 0.10 mL of the composition of the present invention were drawn up with a small volume syringe. This syringe was slowly administered (over 20-30 seconds) via a 3 way stop-cock. 0.50 mL of 0.9% NaCl was drawn up into the same syringe to fully flush the syringe and also administered through the 3 way stop-cock. The composition of the present invention and the flushing medium were collected at the outlet of the catheter. After administration of the composition of the present invention and flushing with medium to the catheter, the system needed to be flushed for 5 min by 0.9% sodium chloride via the perfusor syringe to ensure the complete transfer of the composition of the present invention through the catheter. The amounts per catheter type were pooled and the retinol content was measured by HPLC.

The composition of the present invention was tested according the following test matrix:

Example 4: Local Tolerance for Intravenous and Intramuscular Administration of the Composition According to the Invention The evaluation of local tolerance should be performed following Good Laboratory Practice (GLP) regulations in suitable animals prior to human exposure to the product. The purpose of these studies is to ascertain whether medicinal products are tolerated at injection sites of the body and/or have any other side effects.

Thus, the local tolerance of the composition of the present invention after intravenous and intramuscular administration is tested in a suitable animal model, simulating best the situation in a preterm human infant.

In a preclinical test setting, 3 groups of animals will undergo intravenous and/or intramuscular administration. Group 1 is administered with the composition according to the invention (group 1), Group 2 is being administered an authorised Vitamin A product based on a non-ionic solubizer polysorbate and/or PEG-40 Hydrogenated Castor Oil, and Group 3 is administered vehicle (0.9% sodium chloride) as a control.

Repeated observations of the animals take place particularly prior to and after administration.

A careful macroscopic examination of the injection sites and surrounding tissues as well as a histological examination is carried out. In parallel, plasma samples are taken to assess immune response to the administered products, particularly histamine levels.

Following the above-described experimental procedure, it can be verified that the aqueous pharmaceutical composition according to the present invention exhibits favorable local tolerance upon IV or IM administration. The composition according to the invention is particularly suitable for preterm infants.

| Medical Device/ Test solution | Application of test solution and flushing | Flushing before sampling | No. of tests | Test solution volume | Nominal IU per diluted test solution | Retinol content compared to initial assay in test solution |
|---|---|---|---|---|---|---|
| Umbilicus catheter PUR/inventive composition | 0.10 mL + 0.50 mL (0.9% NaCl) | 5 min at 5 mL/h | 5 | 5 × (0.10 mL + 0.50 mL + 0.4 mL) = 5 mL | 25.000 IU (5 × 5.000 IU) | 100% |
| Umbilicus catheter PVC/inventive composition | 0.10 mL + 0.50 mL (0.9% NaCl) | 5 min at 5 mL/h | 5 | 5 × (0.10 mL + 0.50 mL + 0.4 mL) = 5 mL | 25.000 IU (5 × 5.000 IU) | 98% |
| Umbilicus catheter Silicone/inventive composition | 0.10 mL + 0.50 mL (0.9% NaCl) | 5 min at 5 mL/h | 5 | 5 × (0.10 mL + 0.50 mL + 0.4 mL) = 5 mL | 25.000 IU (5 × 5.000 IU) | 97% |

Despite the generally high lipophilicity of retinol and the lipophilicity of catheter material, the composition of the present invention was found to be neither compromised by sorption to the catheter material (polyurethane, polyvinylchloride, silicone) nor by degradation as simulated in a real life test scenario as used in the neonatal intensive care.

The composition of the present invention is therefore highly suitable to be used with different catheter materials with no significant loss of Vitamin A.

REFERENCES

NPTL1: Brandt, R. B. et al. Serum vitamin A in premature and term neonates (1978), The Journal of Pediatrics (92)101-104.

NPTL2: Inder T. E. et al., Vitamin A and E status in very low birth weight infants: Development of an improved parenteral delivery system1998

NPTL3: Shenai, J. P. et al. (1981). Vitamin A delivery from parenteral alimentation solution. J Pediatr, 99(2), 302-305.

NPTL4: Mactier, H. et al. (2012). Vitamin A supplementation improves retinal function in infants at risk of retinopathy of prematurityThe Journal of Pediatrics, 160(6), 954-959. e1

NPTL5: Peeples et al., Vitamin A status of preterm infants during infancy. (1991) The American Journal of Clinical Nutrition Vol 53(6) 1455-1459

NPTL6: Darlow, B. A. et al. (2016). Vitamin A supplementation to prevent mortality and short- and long-term morbidity in very low birth weight infants. Cochrane Database of Systematic Reviews 2016, Issue 8. Art. No.: CD000501

NPTL7: Mactier, H. (2013). Vitamin A for preterm infants; where are we now Semin Fetal Neonatal Med.

NPTL8: DSM Nutritional Products Ltd. (2015). Product Information—Product Data Sheet—Vitamin A Palmitate 1.7 MIU/g NPTL9: Kuwahara, T. et al. (2013). Effects of lipid emulsion and multivitamins on the growth of microorganisms in peripheral parenteral nutrition solutions. Int J Med Sci, 10(9), 1079-1084.

NPTL10: Kuwahara, T. et al. (2010). Growth of microorganisms in total parenteral nutrition solutions containing lipid. Int J Med Sci, 7(3), 101-109.

NPTL11: Vitamin A Nepalm 100.000 IU/2 ML injectable solution. Package Leaflet. (2014)

NPTL12: British National Formulary 41 Vitamin A Palmitate-Cambridge Pharmaceuticals. 2001

NPTL13: Martindale Pharmacopeia: The Complete Drug Reference. 36th Edition. (2009). Pharmaceutical Press. Section on "Nonionic Surfactants" (pp. 1914-1920).

NPTL14: Pfizer. AQUASOL A™ PARENTERAL (VITAMIN A, RETINOL) Physician Prescribing Information. Revised January 2018

NPTL15: Mystery of the E-Ferol syndrome. Nutrition Reviews 45(3), 76-77.

NPTL16: Graham S. Turner M. European Study of Neonatal Exposure to Excipients (ESNEE) Infant Volume 7 Issue 6 2011

NPTL17: Cuzzolin (2018). Neonates exposed to excipients: concern about safety Journal of Pediatric and Neonatal Individualized Medicine, 7(1):e070112.

NPTL18: Ong et al. Cellular retinol-binding protein (type two) is abundant in human small intestine. The American Journal of Clinical Nutrition, J Lipid Res, 1987, 28(6), 739-745.

NPTL19: Wardle, S. P. et al. (2001). Randomised controlled trial of oral vitamin A supplementation in preterm infants to prevent chronic lung disease, Archives of Disease in Childhood-Fetal and Neonatal Edition 84(1), F9-F13.

NPLT20: Riggle, M. A. et al. (1986). Decrease of available vitamin A in parenteral nutrition solutions. Journal of Parenteral and Enteral Nutrition, 10(4), 388-392.

NPTL21: Losses of vitamin A and E in parenteral nutrition suitable for premature infants. Eur J Clin Nutr, 56(9), 906-912.

NPTL22: Balistreri, W. F. et al. Lessons from the E-Ferol tragedy (1986). Pediatrics, 78(3), 503-506.

NPTL23: Lorenz, W. et al. Histamine release and hypotensive reactions in dogs by solubilizing agents and fatty acids: analysis of various components in cremophor El and development of a compound with reduced toxicity. (1982). Agents Actions, 12(1-2), 64-80.

NPTL24: Mactier, H. (2013). Vitamin A for preterm infants; where are we now. Semin Fetal Neonatal Med, 18(3), 166-171.

NPTL25: Solutol HS15—Technical Information, BASF (2003)

NPTL26: Vitamin A Nepalm, 100.000 IU/2 ml, injectable solution, Summary of Product Characteristics (2008)

NPTL27: AQUASOL A, vitamin A palmitate injection solution, Hospira, Inc., Package Leaflet (2018)

PTL1: WO 2016/188876

PTL2: WO 2016/188874

The invention claimed is:

1. A method of treating or preventing vitamin A deficiency or a vitamin A deficiency-associated disease, the method comprising administering an aqueous pharmaceutical composition to a subject in need thereof, wherein the composition comprises:

retinol or a pharmaceutically acceptable ester thereof, wherein the pharmaceutically acceptable ester of retinol is selected from retinol acetate, retinol propionate, and retinol palmitate;

one or more polyethylene glycol esters of hydroxystearic acid, wherein the one or more polyethylene glycol esters of hydroxystearic acid comprise macrogol-15-hydroxystearate; and one or more pharmaceutically acceptable excipients;

wherein the composition has a pH in the range of about 5.5 to about 7.5;

wherein the retinol or the pharmaceutically acceptable ester thereof and the one or more polyethylene glycol esters of hydroxystearic acid are present as micelles having a mean particle size of about 100 nm or less;

wherein the composition has an osmolality of about 100 to about 600 mOsm/kg;

wherein the composition is administered parenterally; and wherein the composition is a transparent aqueous solution and is free of polysorbate 80.

2. The method according to claim 1, wherein the composition comprises a pharmaceutically acceptable retinol ester which is retinol palmitate.

3. The method according to claim 1, wherein the one or more pharmaceutically acceptable excipients comprise one or more selected from α-tocopherol, β-tocopherol, γ-tocopherol, δ-tocopherol and esters of any one of α-tocopherol, β-tocopherol, γ-tocopherol and δ-tocopherol.

4. The method according to claim 1, wherein the composition comprises ascorbic acid or a pharmaceutically acceptable salt thereof, optionally in combination with one or more selected from: citric acid or a pharmaceutically acceptable salt thereof, and phosphoric acid or a pharmaceutically acceptable salt thereof.

5. The method according to claim 1, wherein the subject is a human infant.

6. The method according to claim 1, wherein the subject is a neonate human infant.

7. The method according to claim 1, wherein the vitamin A deficiency-associated disease is retinopathy of prematurity or is bronchopulmonary dysplasia.

8. The method according to claim 1, wherein the composition is administered intravenously or intramuscularly.

9. The method according to claim 1, wherein the composition is sterile-filtered.

10. The method according to claim 1, wherein the subject is a preterm human infant.

11. The method according to claim 1, wherein said micelles have a mean particle size of 100 nm ±10%, or less.

* * * * *